United States Patent
Lucas et al.

(10) Patent No.: US 12,029,777 B2
(45) Date of Patent: Jul. 9, 2024

(54) SERINE PROTEINASE INHIBITORS: SERP-1 AND SERP-1 RCL-DERIVED PEPTIDES EFFECT ON MICROBIOME COMPOSITION AND USES THEREOF

(71) Applicant: ARIZONA BOARD OF REGENTS ON BEHALF OF ARIZONA STATE UNIVERSITY, Scottsdale, AZ (US)

(72) Inventors: Alexandra Lucas, Tempe, AZ (US); Jordan Yaron, Scottsdale, AZ (US); Efrem Lim, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 220 days.

(21) Appl. No.: 17/422,718

(22) PCT Filed: Jan. 13, 2020

(86) PCT No.: PCT/US2020/013398
§ 371 (c)(1),
(2) Date: Jul. 13, 2021

(87) PCT Pub. No.: WO2020/150168
PCT Pub. Date: Jul. 23, 2020

(65) Prior Publication Data
US 2022/0088117 A1 Mar. 24, 2022

Related U.S. Application Data

(60) Provisional application No. 62/792,201, filed on Jan. 14, 2019.

(51) Int. Cl.
*A61K 38/10* (2006.01)
*A61K 38/00* (2006.01)

(52) U.S. Cl.
CPC ............ *A61K 38/10* (2013.01); *A61K 38/005* (2013.01)

(58) Field of Classification Search
CPC ............................... A61K 38/10; A61K 38/005
See application file for complete search history.

(56) References Cited

U.S. PATENT DOCUMENTS

| 7,419,670 B2 | 9/2008 | Zhong |
| 2011/0009311 A1 | 1/2011 | Roberts |
| 2018/0319868 A1 | 11/2018 | Lucas |

FOREIGN PATENT DOCUMENTS

WO   WO-2016154041 A1 * 9/2016 ............ A61K 38/07

OTHER PUBLICATIONS

Autoimmune Diseases, from Cleveland Clinic, 2021, pp. 1-10.*
Coronavirus, from Cleveland Clinic, 2022, pp. 1-8.*
Saline solution, from https://www.biologyonline.com/dictionary/saline-solution, pp. 1-8, accessed Sep. 12, 2023.*
Ambadapadi et al., "Abstract 19841: Gut Microbiome Influences Immune Modulating Therapy for Inflammatory Vasculitis in a Lethal Herpesviral Infection", Circulation, (Mar. 29, 2018), vol. 134, pp. 1-1, XP055725627.
Ambadapadi Set al: "Serine protease inhibitor (serpin) reactive center loop peptides as therapy for inflammatory vasculitis, hemorrhage and acute viral sepsis", Atherosclerosis, vol. 241, No. 1, Jan. 1, 2015 (Jan. 1, 2015), XP029167679, ISSN: 0021-9150, DOI: 10.1016/J.ATHEROSCLEROSIS.2015.04.994 *abstract *.
Ambadapadi, S. et al. Reactive Center Loop (RCL) peptides derived from serpins display independent coagulation and immune modulating activities. J. Biol. Chem. 291, 2874-2887 (2016).
Badawi, A. H. & Siahaan, T. J. Immune modulating peptides for the treatment and suppression of multiple sclerosis. Clin. Immunol. 144, 127-138 (2012).
Bajaj, J. S. et al. Fecal microbiota transplant from a rational stool donor improves hepatic encephalopathy: a randomized clinical trial. Hepatology 66, 1727-1738 (2017).
Baldridge, M. T. et al. Commensal microbes and interferon-λ determine persistence of enteric murine norovirus infection. Science: 347, 266-269 (2015).
Bédos, J.-P. et al. Pharmacodynamic activities of ciprofloxacin and sparfloxacin in a murine pneumococcal pneumonia model: Relevance for drug efficacy. J. Pharmacol. Exp. Ther. 286, 29-35 (1998).
Blander, J. M., Longman, R. S., Iliev, I. D., Sonnenberg, G. F. & Artis, D. Regulation of inflammation by microbiota interactions with the host. Nat. Immunol. 18, 851-860 (2017).
Bolyen, E. et al. QIIME 2: Reproducible, interactive, scalable, and extensible microbiome data science. PeerJ Prepr. 6, e27295v1 (2018).
Brunel, A., Influence of the destabilisation of the maternal digestive microflora on that of the newborn rat. Biol. Neonate 63, 236-245 (1993).
Budden, K. F. et al. Emerging pathogenic links between microbiota and the gut-lung axis. Nat. Rev. Microbiol. 15, 55-63 (2017).
Caporaso, J. G. et al. Global patterns of 16S rRNA diversity at a depth of millions of sequences per sample. Proc. Natl. Acad. Sci. 108, 4516-4522 (2011).

(Continued)

*Primary Examiner* — Li N Komatsu
(74) *Attorney, Agent, or Firm* — BOOTH UDALL FULLER, PLC

(57) ABSTRACT

Disclosed herein is are methods of preventing, reducing or inhibiting a viral or immune disorder, comprising administering to a subject at risk or that has acquired a viral or immune disorder an effective amount of a composition comprising a polypeptide derived from a reactive center loop of a serine protease inhibitor or a biologically active variant thereof, wherein the subject has not been administered antibiotics within at least one day of administering the composition. Also disclosed are compositions and kits for preventing, reducing or inhibiting a viral or immune disorder.

9 Claims, 28 Drawing Sheets
(3 of 28 Drawing Sheet(s) Filed in Color)
Specification includes a Sequence Listing.

(56) References Cited

OTHER PUBLICATIONS

Cardin, R. D., Brooks, J. W., Sarawar, S. R. & Doherty, P. C. Progressive loss of CD8+ T cell-mediated control of a gammaherpesvirus in the absence of CD4+ T cells. J. Exp. Med. 184, 863-71 (1996).
Carlson, J. A., Perlmutter, A., Tobin, E., Richardson, D. & Rohwedder, A. Adverse antibiotic-induced eruptions associated with epstein barr virus infection and showing Kikuchi-Fujimoto disease-like histology. Am. J. Dermatopathol. 28, 48-55 (2006).
Chen, H. et al. Analysis of In Vivo Serpin Functions in Models of Inflammatory Vascular Disease. Methods Mol. Biol. 1826, 157-182 (2018).
Chen, H. et al. Mouse gamma herpesvirus MHV-68 induces severe gastrointestinal (GI) dilatation in interferon gamma receptor-deficient mice (IFNγR−/−) that is blocked by interleukin-10. Viruses 10, (2018).
Chen, H. et al. Myxomavirus-derived serpin prolongs survival and reduces inflammation and hemorrhage in an unrelated lethal mouse viral infection. Antimicrob. Agents Chemother. 57, 4114-4127 (2013).
Chen, X. et al. The cardiovascular macrophage: a missing link between gut microbiota and cardiovascular diseases? Eur Rev Med Pharmacol Sci 22, 1860-1872 (2018).
Coen, N. et al. Activity and Mechanism of Action of HDVD, a Novel Pyrimidine Nucleoside Derivative with High Levels of Selectivity and Potency against Gammaherpesviruses. J. Virol. 87, 3839-3851 (2013).
Costola-de-Souza, C. et al. Monoacylglycerol Lipase (MAGL) Inhibition Attenuates Acute Lung Injury in Mice. PLoS One 8, 1-15 (2013).
Dal Canto, A. J., Swanson, P. E., O'Guin, A. K., Speck, S. H. & Virgin, H. W. IFN-gamma action in the media of the great elastic arteries, a novel immunoprivileged site. J. Clin. Invest. 107, R15-22 (2001).
DeSantis, T. Z. et al. Greengenes, a chimera-checked 16S rRNA gene database and workbench compatible with ARB. Appl. Environ. Microbiol. 72, 5069-5072 (2006).
Ehlers, M. R. Immune-modulating effects of alpha-1 antitrypsin. Biol. Chem. 395, 1187-1193 (2014).
Elefante, E. et al. One year in review 2017: systemic vasculitis. Clin. Exp. Rheumatol. 35 Suppl 1, 5-26 (2017).
Elefante, E. et al. One year in review 2018: systemic vasculitis. Clin. Exp. Rheumatol. 36 Suppl 1, 12-32 (2018).
Elefante, E., Tripoli, A., Ferro, F. & Baldini, C. One year in review: systemic vasculitis. Clin. Exp. Rheumatol. 34, S1-6 (2016).
Fei, R. et al. Anti-inflammatory activity of a thermophilic serine protease inhibitor from extremophile Pyrobaculum neutrophilum. Eur. J. Inflamm. 15, 143-151 (2017).
Finlay and McFadden, Anti-Immunology: Evasion of the Host Immune System by Bacterial and Viral Pathogens, Cell 2006.
Flano, E., Husain, S. M., Sample, J. T., Woodland, D. L. & Blackman, M. A. Latent Murine -Herpesvirus Infection Is Established in Activated B Cells, Dendritic Cells, and Macrophages. J. Immunol. 165, 1074-1081 (2000).
Florquin, S. et al. Release of urokinase plasminogen activator receptor during urosepsis and endotoxemia. Kidney Int. 59, 2054-2061 (2001).
Gopalakrishnan, V. et al. Gut microbiome modulates response to anti-PD-1 immunotherapy in melanoma patients. Science (80 -. ). 359, 97-103 (2018).
Hanaoka, M. et al. Immunomodulatory strategies prevent the development of autoimmune emphysema. Respir. Res. 11, 179 (2010).
Handley, S. A. The virome: a missing component of biological interaction networks in health and disease. Genome Med. 8, 32-34 (2016).
Harada, T. et al. *Enterococcus saigonensis* sp. nov., isolated from retail chicken meat and liver. Int. J. Syst. Evol. Microbiol. 66, 3779-3785 (2016).

Hatemi, I., Hatemi, G. & Çelik, A. F. Systemic vasculitis and the gut. Curr. Opin. Rheumatol. 29, 33-38 (2017).
Hevia, A. et al. Intestinal dysbiosis associated with systemic lupus erythematosus. MBio 5, 1-10 (2014).
Ildefonso, C. J. et al. Gene Delivery of a Viral Anti-Inflammatory Protein to Combat Ocular Inflammation. Hum. Gene Ther. 26, 59-68 (2015).
Imhann, F. et al. Proton pump inhibitors affect the gut microbiome. Gut 65, 740-748 (2016).
Jones, M. K. et al. Enteric bacteria promote human and mouse norovirus infection of B cells. Science. 346, 755-759 (2014).
Kanai, K. et al. Murine γ-Herpesvirus 68 Induces Severe Lung Inflammation in IL-27-Deficient Mice with Liver Dysfunction Preventable by Oral Neomycin. J. Immunol. 200, 2703-2713 (2018).
Kasselman, L. J., Vernice, N. A., DeLeon, J. & Reiss, A. B. The gut microbiome and elevated cardiovascular risk in obesity and autoimmunity. Atherosclerosis 271, 203-213 (2018).
Keita, M. B. et al. Non-contiguous finished genome sequence and description of *Bacillus massiliogorillae* sp. nov. Stand. Genomic Sci. 9, 93-105 (2013).
Kotra, L. P., Haddad, J. & Mobashery, S. Aminoglycosides: Perspectives on mechanisms of action and resistance and strategies to counter resistance. Antimicrob. Agents Chemother. 44, 3249-3256 (2000).
Kwiecien, J. M. et al. Myxoma virus derived immune modulating proteins, M-T7 and Serp-1, reduce early inflammation after spinal cord injury in the rat model. Folia Neuropathol. 57, 41-50 (2019).
Lee, S. D. *Frondihabitans peucedani* sp. nov., an actinobacterium isolated from rhizosphere soil, and emended description of the genus *Frondihabitans* Greene et al. 2009. Int. J. Syst. Evol. Microbiol. 60, 1740-1744 (2010).
Liqiang Zhang, Jordan R. Yaron, Sriram Ambadapadi, Alexandra Lucas, "Viral Serpin Reactive Center Loop (RCL) Peptides: Design and Testing", Liqiang Zhang ,Jordan R. Yaron , Sriram Ambadapadi , Alexandra Lucas, Lucas, Alexandra, Serpins : Methods and Protocols, US, Springer Science+Business Media, LLC, (Sep. 8, 2018), vol. 1826, pp. 133-142, doi: 10.1007/978-1-4939-8645-3_9, ISSN 1064-3745, ISBN 978-1-60761-961-1, XP009528939.
Love, M. I., Huber, W. & Anders, S. Moderated estimation of fold change and dispersion for RNA-seq data with DESeq2. Genome Biol. 15, 1-21 (2014).
Lucas, A., Yaron, J. R., Zhang, L., Macaulay, C. & McFadden, G. Serpins: Development for Therapeutic Applications. Methods Mol. Biol. 1826, 255-265 (2018).
Luzzatto, L., Apirion, D. & Schlessinger, D. Mechanism of action of streptomycin in *E. coli*: interruption of the ribosome cycle at the initiation of protein synthesis. Proc. Natl. Acad. Sci. U. S. A. 60, 873-80 (1968).
Mahon et al. "Crystal Structure of Cleaved Serp-1, a Myxomavirus-Derived Immune Modulating Serpin: Structural Design of Serpin Reactive Center Loop Peptides with Improved Therapeutic Function," Biochemistry, Dec. 11, 2017 (Dec. 11, 2017), vol. 57, Iss. 7, pp. 1096-1107. entire document.
Mahon et al., "Crystal Structure of Cleaved Serp-1, a Myxomavirus-Derived Immune Modulating Serpin: Structural Design of Serpin Reactive Center Loop Peptides with Improved Therapeutic Function", Biochemistry, (Dec. 11, 2017), vol. 57, No. 7, pp. 1096-1107, XP055725628.
Maldonado, J., Yaron, J. R., Zhang, L. & Lucas, A. Next-Generation Sequencing Library Preparation for 16S rRNA Microbiome Analysis After Serpin Treatment. Methods Mol. Biol. 1826, 213-221 (2018).
Matson, V. et al. The commensal microbiome is associated with anti-PD-1 efficacy in metastatic melanoma patients. Science (80 -. ). 359, 104-108 (2018).
Miller, L. W. et al. Inhibition of transplant vasculopathy in a rat aortic allograft model after infusion of anti-inflammatory viral serpin. Circulation 101, 1598-605 (2000).
Mora, A. L. et al. Lung infection with γ-herpesvirus induces progressive pulmonary fibrosis in Th2- biased mice. Am. J. Physiol. Cell. Mol. Physiol. 289, L711-L721 (2005).

(56) References Cited

OTHER PUBLICATIONS

Nash, P., Whitty, A., Handwerker, J., Macen, J. & McFadden, G. Inhibitory specificity of the anti-inflammatory myxoma virus serpin, SERP-1. J. Biol. Chem. 273, 20982-20991 (1998).
Olivadoti, M., Toth, L. A., Weinberg, J. & Opp, M. R. Murine gammaherpesvirus 68: a model for the study of Epstein-Barr virus infections and related diseases. Comp. Med. 57, 44-50 (2007).
Organ, L. et al. Structural and functional correlations in a large animal model of bleomycin-induced pulmonary fibrosis. BMC Pulm. Med. 15, (2015).
Pedro Simas, J. & Efstathiou, S. Murine gammaherpesvirus 68: a model for the study of gammaherpesvirus pathogenesis. Trends Microbiol. 6, 276-282 (1998).
Ramezani, A. & Raj, D. S. The Gut Microbiome, Kidney Disease, and Targeted Interventions. J. Am. Soc. Nephrol. 25, 657-670 (2014).
Ritschel, W. A. Biological Half-Lives of Drugs. Drug Intell. Clin. Pharm. 4, 332-347 (1970).
Rodo, X. et al. Tropospheric winds from northeastern China carry the etiologic agent of Kawasaki disease from its source to Japan. Proc. Natl. Acad. Sci. 111, 7952-7957 (2014).
Routy, B. et al. Gut microbiome influences efficacy of PD-1-based immunotherapy against epithelial tumors. Science. 359, 91-97 (2018).
Ryan, J. L. et al. Epstein-barr virus infection is common in inflamed gastrointestinal mucosa. Dig. Dis. Sci. 57, 1887-1898 (2012).
Sanders, C. C. Ciprofloxacin: In Vitro Activity, Mechanism of Action, and Resistance. Clin. Infect. Dis. 10, 516-527 (1988).
Scheperjans, F. et al. Gut microbiota are related to Parkinson's disease and clinical phenotype. Mov. Disord. 30, 350-358 (2015).
Scher, J. U. et al. Expansion of intestinal Prevotella copri correlates with enhanced susceptibility to arthritis. Elife 2013, 1-20 (2013).
Schindelin, J. et al. Fiji: an open-source platform for biological-image analysis. Nat. Methods 9, 676-682 (2012).
Schirmer, M. et al. Linking the Human Gut Microbiome to Inflammatory Cytokine Production Capacity. Cell 167, 1125-1136.e8 (2016).
Segata, N. et al. Metagenomic biomarker discovery and explanation. Genome Biol. 12, (2011).
Singh, V., Yeoh, B. S. & Vijay-Kumar, M. Gut microbiome as a novel cardiovascular therapeutic target. Curr. Opin. Pharmacol. 27, 8-12 (2016).
Soowamber, M., Weizman, A. V. & Pagnoux, C. Gastrointestinal aspects of vasculitides. Nat. Rev. Gastroenterol. Hepatol. 14, 185-194 (2017).
Sparks-Thissen, R. L. et al. CD4 T cell control of acute and latent murine gammaherpesvirus infection requires IFNγ. Virology 338, 201-208 (2005).
Sparks-Thissen, R. L., Braaten, D. C., Kreher, S., Speck, S. H. & Virgin, H. W. An optimized CD4 T-cell response can control productive and latent gammaherpesvirus infection. J. Virol. 78, 6827-35 (2004).
Spiekerkoetter, E. et al. Reactivation of gammaHV68 induces neointimal lesions in pulmonary arteries of S100A4/Mts1-overexpressing mice in association with degradation of elastin. Am.J.Physiol Lung Cell Mol.Physiol 294, L276-L289 (2008).
Stone, K. J. & Strominger, J. L. Mechanism of Action of Bacitracin: Complexation with Metal Ion and C55-Isoprenyl Pyrophosphate. Proc. Natl. Acad. Sci. 68, 3223-3227 (1971).
Stünkel, K. G. E., Hewlett, G. & Zeiler, H. J. Ciprofloxacin enhances T cell function by modulating interleukin activities. Clin. Exp. Immunol. 86, 525-531 (1991).
Swenson, C. E., Stewart, K. A., Hammett, J. L., Fitzsimmons, W. E. & Ginsberg, R. S. Pharmacokinetics and in vivo activity of liposome-encapsulated gentamicin. Antimicrob. Agents Chemother. 34, 235-240 (1990).
Tardif, J.-C. et al. A randomized controlled, phase 2 trial of the viral serpin Serp-1 in patients with acute coronary syndromes undergoing percutaneous coronary intervention. Circ. Cardiovasc. Interv. 3, 543-8 (2010).
Thackray, L. B. et al. Oral Antibiotic Treatment of Mice Exacerbates the Disease Severity of Multiple Flavivirus Infections. Cell Rep. 22, 3440-3453.e6 (2018).
Tripathi, A. et al. The gut-liver axis and the intersection with the microbiome. Nat. Rev. Gastroenterol. Hepatol. 15, 397-411 (2018).
Vetizou, M. et al. Anticancer immunotherapy by CTLA-4 blockade relies on the gut microbiota. Science. 350, 1079-1084 (2015).
Viswanathan, K. et al. Myxoma viral serpin, Serp-1, a unique interceptor of coagulation and innate immune pathways. Thromb. Haemost. 95, 499-510 (2006).
Viswanathan, K. et al. Myxoma viral serpin, Serp-1, inhibits human monocyte adhesion through regulation of actin-binding protein filamin B. J. Leukoc. Biol. 85, 418-26 (2009).
Vrieze, A. et al. Transfer of intestinal microbiota from lean donors increases insulin sensitivity in individuals with metabolic syndrome. Gastroenterology 143, 913-916.e7 (2012).
Wakefield, A. J. et al. Detection of herpesvirus DNA in the large intestine of patients with ulcerative colitis and Crohn's disease using the nested polymerase chain reaction. J. Med. Virol. 38, 183-190 (1992).
Walters, A. W., Albe, J. R. et al. Vascular permeability in the brain is a late pathogenic event during Rift Valley fever virus encephalitis in rats. Virology 526, 173-179 (2019).
Weck, K. E. et al. Murine gamma-herpesvirus 68 causes severe large-vessel arteritis in mice lacking interferon-gamma responsiveness: a new model for virus-induced vascular disease. Nat. Med. 3, 1346-53 (1997).
Winkler, C. W., Race, B., Phillips, K. & Peterson, K. E. Capillaries in the olfactory bulb but not the cortex are highly susceptible to virus-induced vascular leak and promote viral neuroinvasion. Acta Neuropathol. 130, 233-245 (2015).
Wise et al.,"Inflammatory Diseases and Viral Immune Modulating Protein Therapeutics," Journal of Clinical Medicine (ISSN 2077-0383), 2019.
Wymore Brand, M. et al. The Altered Schaedler Flora: Continued Applications of a Defined Murine Microbial Community. ILAR J. 56, 169-178 (2015).
Xie, Z. et al. Vascular endothelial hyperpermeability induces the clinical symptoms of Clarkson disease (the systemic capillary leak syndrome). Blood 119, 4321-4332 (2012).
Yanai, H., Nagasaki, S., Okita, K., Mitani, N., Shimizu, N. & Epstein-Barr virus infection of the colon with inflammatory bowel disease. Am. J. Gastroenterol. 94, 1582-1586 (2004).
Yang, J. H. et al. Antibiotic-Induced Changes to the Host Metabolic Environment Inhibit Drug Efficacy and Alter Immune Function. Cell Host Microbe 22, 1-9 (2017).
Yaron et al., "Immune protection is dependent on the gut microbiome in a lethal mouse gammaherpesviral infection", Scientific Reports, (Feb. 11, 2020), vol. 10, No. 2371, pp. 1-13, XP055725632.
Zhang, L. et al. A Virus-Derived Immune Modulating Serpin Accelerates Wound Closure with Improved Collagen Remodeling. J. Clin. Med. 8, 1626 (2019).

\* cited by examiner

FIG. 1A

S-7: G₃₀₅TTASSDTAITLIPR₃₁₉  SEQ ID NO: 2

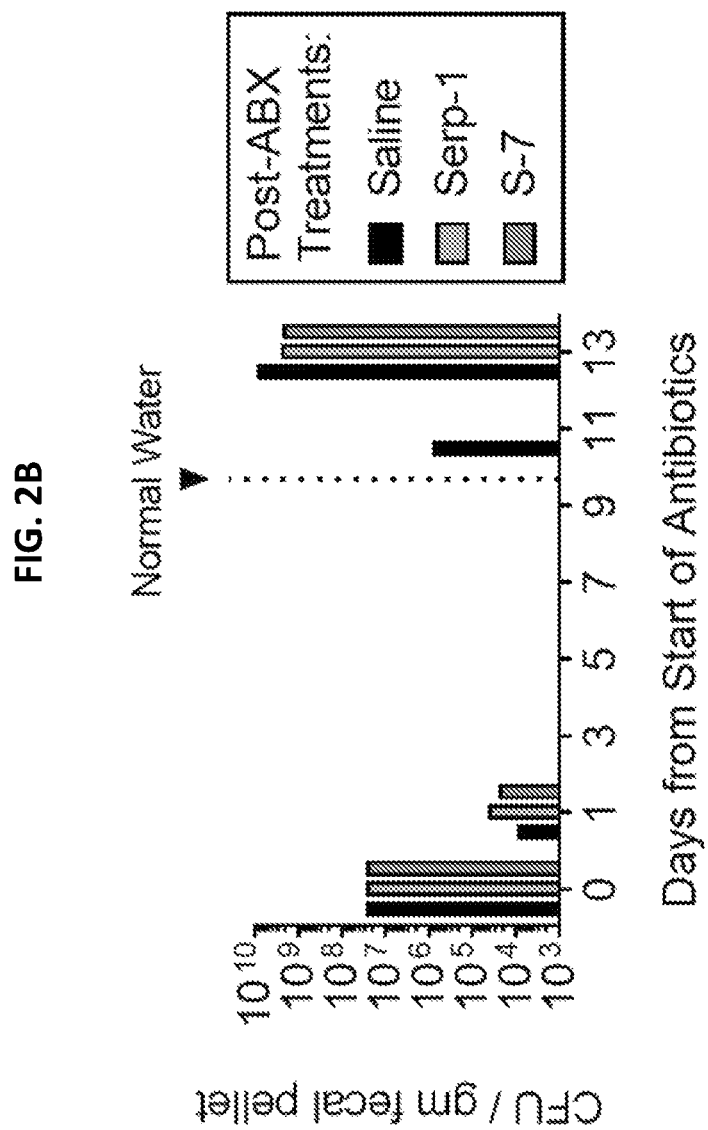

FIG. 7C

Discriminant ASV analyses between Serp-1 (No Abx) vs Saline (No Abx)

| ASV | Taxonomic assignment (most closely related taxa) | Likelihood | DeSeq2 | Lefse | |
|---|---|---|---|---|---|
| ASV357 | p_Actinobacteria;c_Actinobacteria;o_Bifidobacteriales;f_Bifidobacteriaceae;g_Bifidobacterium;s_Bifidobacterium longum | . | x | . | Associated with Serp-1 (No Abx) |
| ASV49 | p_Firmicutes;c_Bacilli;o_Bacillales;f_Bacillaceae;g_Bacillus;s_Bacillus massiliogorillae | x | . | . | |
| ASV6 | p_Firmicutes;c_Clostridia;o_Clostridiales;f_Clostridiaceae;g_Clostridium;s_Clostridium saudiense | . | x | x | |
| ASV19 | p_Firmicutes;c_Clostridia;o_Clostridiales;f_Clostridiaceae;g_Clostridium;s_Clostridium saudiense | . | x | . | |
| ASV22 | p_Firmicutes;c_Clostridia;o_Clostridiales;f_Clostridiaceae;g_Clostridium;s_Clostridium saudiense | . | x | . | |
| ASV37 | p_Firmicutes;c_Clostridia;o_Clostridiales;f_Peptostreptococcaceae;g_Romboutsia;s_Romboutsia timonensis | . | x | . | |
| ASV36 | p_Firmicutes;c_Clostridia;o_Clostridiales;f_Peptostreptococcaceae;g_Romboutsia;s_Romboutsia timonensis | . | x | . | |
| ASV111 | p_Firmicutes;c_Clostridia;o_Clostridiales;f_Peptostreptococcaceae;g_Romboutsia;s_Romboutsia timonensis | . | x | . | |
| ASV498 | p_Proteobacteria;c_Betaproteobacteria;o_Burkholderiales;f_Burkholderiaceae;g_Limnohabitans;s_Limnohabitans australis | . | x | . | |
| ASV168 | p_Proteobacteria;c_Betaproteobacteria;o_Burkholderiales;f_Comamonadaceae;g_Pelomonas;s_Pelomonas aquatica | . | x | . | |
| ASV40 | p_Proteobacteria;c_Gammaproteobacteria;o_Enterobacteriales;f_Enterobacteriaceae;g_Escherichia;s_Escherichia marmotae | . | x | . | |
| ASV129 | p_Actinobacteria;c_Actinobacteria;o_Micrococcales;f_Micrococcaceae;g_Micrococcinineae;s_Frigoribacterium pararoseum | x | . | . | Associated with Saline (No Abx) |
| ASV2 | p_Firmicutes;c_Bacilli;o_Bacillales;f_Paenibacillaceae;g_Brevibacillus;s_Brevibacillus reuszeri | . | x | . | |
| ASV1 | p_Firmicutes;c_Bacilli;o_Lactobacillales;f_Enterococcaceae;g_Enterococcus;s_Enterococcus saigonensis | . | . | x | |

FIG. 7D

Discriminant ASV analyses between S-7 (No Abx) vs Saline (No Abx)

| ASV | Taxonomic assignment (most closely related taxa) | Likelihood | DeSeq2 | Lefse | |
|---|---|---|---|---|---|
| ASV44 | p_Firmicutes;c_Bacilli;o_Bacillales;f_Bacillaceae;g_Bacillus;s_Bacillus massiliogorillae | x | . | . | Associated with S-7 (No Abx) |
| ASV137 | p_Actinobacteria;c_Actinobacteria;o_Micrococcales;f_Microbacteriaceae;g_Microbacterineae;s_Frondihabitans peucedani | x | . | . | Associated with Saline (No Abx) |
| ASV1 | p_Firmicutes;c_Bacilli;o_Lactobacillales;f_Enterococcaceae;g_Enterococcus;s_Enterococcus saigonensis | . | . | x | |

Discriminant ASV analyses between Serp-1 (No Abx) and S-7 (No Abx) vs Saline (No Abx)

| ASV | Taxonomic assignment (most closely-related taxa) | Likelihood | DeSeq2 | LsfSe | |
|---|---|---|---|---|---|
| ASV7 | p_Firmicutes;o_Bacillales;f_Bacillaceae;g_Bacillus;s_Bacillus massiliogorillae | x | . | . | Associated with Serp-1 and S-7 (No Abx) |
| ASV5 | p_Firmicutes;c_Erysipelotrichia;o_Erysipelotrichales;f_Erysipelotrichaceae;g_Turicibacter;s_Turicibacter sanguinis | . | x | . | |
| ASV6 | c_Firmicutes;o_Clostridia;o_Clostridiales;f_Clostridiaceae;g_Clostridium;s_Clostridium saudense | . | x | . | |
| ASV25 | p_Firmicutes;o_Erysipelotrichia;o_Erysipelotrichales;f_Erysipelotrichaceae;g_Turicibacter;s_Turicibacter sanguinis | . | x | . | |
| ASV19 | p_Firmicutes;c_Clostridia;o_Clostridiales;f_Clostridiaceae;g_Clostridium;s_Clostridium saudense | . | x | . | |
| ASV22 | p_Firmicutes;c_Clostridia;o_Clostridiales;f_Clostridiaceae;g_Clostridium;s_Clostridium saudense | . | x | . | |
| ASV36 | p_Firmicutes;c_Clostridia;o_Clostridiales;f_Peptostreptococcaceae;g_Romboutsia;s_Romboutsia timonensis | . | x | . | |
| ASV37 | p_Firmicutes;c_Clostridia;o_Clostridiales;f_Peptostreptococcaceae;g_Romboutsia;s_Romboutsia timonensis | . | x | . | |
| ASV124 | p_Firmicutes;c_Bacilli;o_Bacillales;f_Bacillaceae;g_Bacillus;s_Bacillus westmanii | . | x | . | |
| ASV3 | p_Firmicutes;c_Bacilli;o_Bacillales;f_Bacillaceae;g_Bacillus;s_Bacillus westmanii | . | x | . | |
| ASV125 | p_Actinobacteria;c_Actinobacteria;o_Micrococcales;f_Microbacteriaceae;g_Frondihabitans;s_Frondihabitans peucedani | x | . | . | |
| ASV171 | p_Cyanobacteria;c_NA;o_Oscillatoriales;f_Microcoleaceae;g_Arthrospira;s_Arthrospira platensis | x | . | . | Associated with Saline (No Abx) |
| ASV406 | p_Proteobacteria;c_Gammaproteobacteria;o_Pseudomonadales;f_Moraxellaceae;g_Acinetobacter;s_Acinetobacter vivianii | x | . | . | |
| ASV164 | p_Cyanobacteria;c_NA;o_Oscillatoriales;f_Microcoleaceae;g_Arthrospira;s_Arthrospira platensis | x | . | . | |
| ASV142 | p_Actinobacteria;c_Actinobacteria;o_Micrococcales;f_Microbacteriaceae;g_Curtobacterium;s_Curtobacterium flaccumfaciens | . | . | x | |
| ASV1 | p_Firmicutes;c_Bacilli;o_Lactobacillales;f_Enterococcaceae;g_Enterococcus;s_Enterococcus adoratenensis | . | . | x | |
| ASV336 | p_Proteobacteria;c_Gammaproteobacteria;o_Pseudomonadales;f_Moraxellaceae;g_Moraxella;s_Moraxella osloensis | . | . | x | |

FIG. 7E

SERINE PROTEINASE INHIBITORS: SERP-1 AND SERP-1 RCL-DERIVED PEPTIDES EFFECT ON MICROBIOME COMPOSITION AND USES THEREOF

CROSS REFERENCE TO RELATED APPLICATION

This application is the U.S. National Stage of International Application No. PCT/US2020/013398, filed Jan. 13, 2020, which claims the benefit of the earlier filing date of U.S. Provisional Application No. 62/792,201, filed Jan. 14, 2019, the contents of each of which are hereby incorporated by reference in their entireties.

ACKNOWLEDGMENT OF GOVERNMENT SUPPORT

This invention was made with government support under AI100987 and HL100202 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 12, 2020, is named 131849-252219_SL.txt and is 6,265 bytes in size.

FIELD

This disclosure relates to serine proteinase inhibitors and methods of use and in particular, to Serp-1 compositions and derivatives thereof, including active fragments, such as Serp-1 RCL-derived peptide S-7, and methods of improving survival in vasculitis, such as murine gammaherpsevirus 68 (MHV68) lethal vasculitis.

BACKGROUND

Viral infections induce potent immune responses, an immunopathogenesis that can lead to severe complications with sepsis or leaky capillary syndromes, excess clotting and bleeding and very high mortality with limited effective treatments, a true unmet clinical need. Sepsis has an associated risk of disseminated intravascular coagulation (DIC) with thrombosis, hemorrhage and shock. One such group of viruses with known severe complications are the gammaherpesviruses (GHV). The murine gammaherpesvirus-68 (MHV-68) is a widely used, well-controlled laboratory model of GHV host-pathogen interaction with genetic similarity to the human viruses Epstein-Barr virus (EBV) and Kaposi's sarcoma-associated herpesvirus (KSHV).

Inflammatory vasculitic syndromes (IVS) are a group of rare, heterogeneous and devastating inflammatory conditions of the body's extensive system of blood vessels with increased morbidity, including sudden loss of vision, aneurysm, aortic arch syndrome, stroke, and associated increases in mortality. The etiology of many systemic vasculitides is currently unknown, with proposed mechanisms ranging from induction by fungal spores to herpesviruses infections (e.g., zoster). A lethal IVS large vessel arteritis model which closely mimics human Giant Cell Arteritis, Kawasaki's disease and Takayasu's arteritis can be induced by high dose intraperitoneal MHV-68 infection of interferon gamma receptor knockout (IFNγR$^{-/-}$) mice. Many infected mice display extensive pulmonary hemorrhage and consolidation, mimicking DIC in viral sepsis, which has a very high attendant mortality. A significant number of mice also have marked colon dilatation reminiscent of toxic megacolon, in addition to aggressive inflammatory cell invasion with hemorrhagic lung consolidation. Herpesvirus infections have been associated with inflammatory bowel diseases and gastrointestinal involvement in systemic vasculitides has been reported.

SUMMARY

Disclosed herein are compositions, methods and kits for preventing, reducing or inhibiting a viral or immune disorder.

In some embodiments, a method of preventing, reducing or inhibiting a viral or immune disorder, comprises administering to a subject at risk or that has acquired a viral or immune disorder an effective amount of a composition comprising a polypeptide derived from a reactive center loop of a serine protease inhibitor or a biologically active variant thereof, wherein the subject has not been administered antibiotics within at least one day of administering the composition.

In some embodiments, the polypeptide has an amino acid sequence with at least 95% sequence identity to the amino acid sequence set forth as SEQ ID NO: 2 or SEQ ID NO:1.

In some embodiments, the polypeptide has the amino sequence with at least 99% sequence identity to the amino acid sequence set forth as SEQ ID NO: 2 or SEQ ID NO:1.

In some embodiments, the polypeptide has the amino acid sequence set forth as GTTASSDTAITLIPR (SEQ ID NO: 2).

In some embodiments, the composition further comprises a carrier, such as 0.9% normal saline, or Citrate-buffered saline (CBS), or Phosphate-buffered saline (PBS), or Ringer's Lactate solution (RL), or Acetated Ringer's solution (AR), or 5% or 10% dextrose in normal saline (D5NS, D10NS), or 5% or 10% dextrose in half-normal saline (D5HNS, D10HNS), or Hank's balanced salt solution (HBSS), or Earle's balanced salt solution (EBSS), or Gey's balanced salt solution (GBSS), or TRIS-buffered saline (TBS), or HEPES-buffered saline (HBS).

In some embodiments, administering comprises one or more of the following routes of administration: subcutaneous, intravenous or intramuscular.

In some embodiments, the viral or immune disorder is a gammaherpesviruses (GHV), Epstein-Barr virus (EBV) and/or Kaposi's sarcoma-associated herpesvirus (KSHV).

In some embodiments, the GHV is murine gammaherpesvirus-68 (MHV-68).

In some embodiments, the GHV is acute or chronic GHV infection.

In some embodiments, the immune disorder is an inflammatory vasculitic syndrome (IVS).

In some embodiments, the composition increases protective gut microbiota and/or decreases patho-exacerbative gut microbiota.

In some embodiments, the protective gut microbiota comprise ASV4 microbiota and patho-exacerbative gut microbiota comprise ASV1 and ASV123.

In some embodiments, a kit for preventing, reducing or inhibiting a viral or immune disorder in a subject at risk or that has acquired a viral or immune disorder is disclosed, comprising a composition comprising a polypeptide derived from a reactive center loop of a serine protease inhibitor or a biologically active variant thereof and instructions of use wherein the instructions indicate the subject must not have been administered antibiotics within at least one day of using the kit.

In some embodiments, a method of altering a gut microbiome is disclosed, comprising administering to a subject in need thereof an effective amount of a composition comprising a polypeptide derived from a reactive center loop of a serine protease inhibitor or a biologically active variant thereof, wherein the subject has not been administered antibiotics within at least one day of administering the composition, and the composition increases protective gut microbiota and/or decreases patho-exacerbative gut microbiota.

In some embodiments, the protective gut microbiota comprise ASV4 microbiota and patho-exacerbative gut microbiota comprise ASV1 and ASV123.

The foregoing and other features of the disclosure will become more apparent from the following detailed description, which proceeds with reference to the accompanying figures.

BRIEF DESCRIPTION OF FIGURES

The patent or application file contains at least one drawing executed in color. Copies of this patent or patent application publication with color drawing(s) will be provided by the Office upon request and payment of the necessary fee.

Figure 1A:
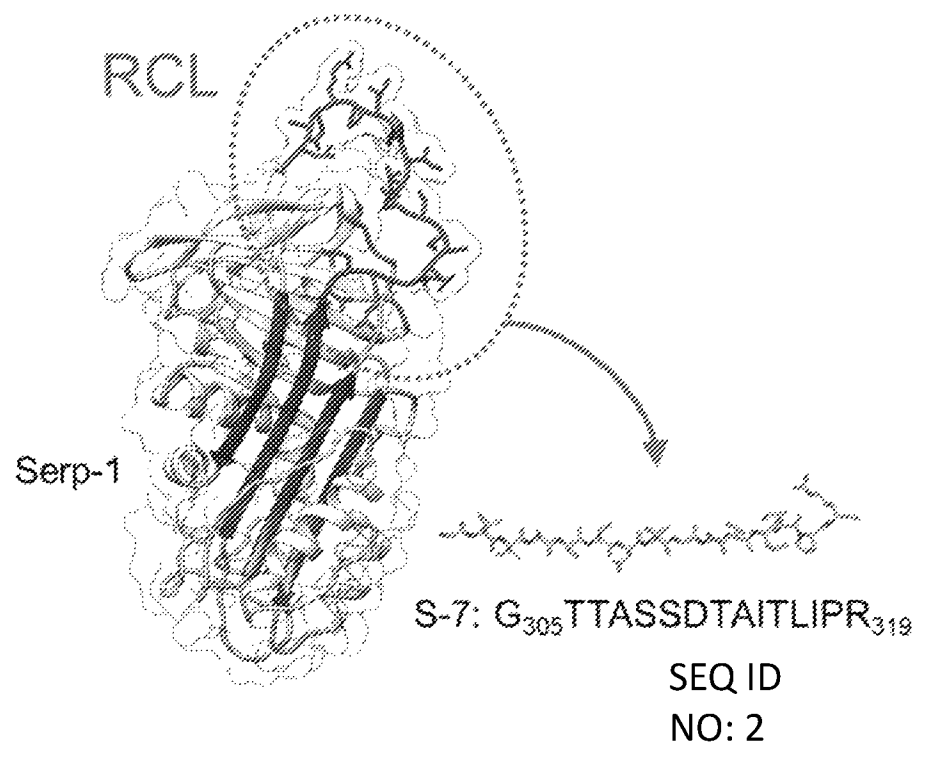

FIG. 1A provides the chemical structure of Serp-1 with A-beta sheet and reactive center loop (RCL) highlighted. RCL-derived peptide S-7 is also provided.

FIGS. 2A-2E show antibiotic treatment accelerates MHV-68 lethality and alters the gut bacterial microbiome. FIG. 2A provides an overview of experimental design. Mice are treated with a broad-spectrum antibiotic cocktail in their drinking water for 10 days, placed on normal water for 1 day, infected with MHV-68 with or without treatments with follow-up for survival. FIG. 2B illustrates antibiotic-medicated water completely ablates bacterial microbiome contents during the course of the 10-day pre-treatment, which recovers by three days after removal of antibiotics. FIG. 2C illustrates 16S microbiome relative abundance (genus level) and FIG. 2D bacterial alpha diversity (Shannon Index) is shown for saline-treated mice with and without antibiotics. FIG. 2E is a heatmap showing ASV abundance in mice treated with saline in the presence or absence of antibiotic pre-treatment.

FIG. 3A shows 16S microbiome relative abundance (genus level). FIG. 3B shows bacterial alpha diversity (Shannon Index). Statistical significance was assessed by Mann-Whitney test. FIG. 3C provides a principal coordinate analysis (PCoA) plot of weighted UniFrac distances. FIG. 3D provides a heatmap showing ASV abundance in mice treated with saline, Serp-1 or S7, in the absence of antibiotics. ASV shown were identified by differential analyses to be associated with Serp-1 or S7 (top section), or saline (bottom section). FIG. 3E provides heatmaps of differential ASV from FIG. 3D compared in the absence or presence of antibiotics for Serp-1 treated mice (left) or S-7 treated mice (right).

FIG. 3F shows relative abundance of ASV4 (identified as differentially associated with Serp-1 and S-7 treatment), and ASV1 and 123 (identified as differentially associated with saline) in individual mouse microbiomes. ASV taxonomic classification of the most closely related bacterial taxa are shown. Saline+Abx, N=6; Saline No Abx, N=6; Serp-1+Abx, N=6; Serp-1 No Abx, N=5; S7+Abx, N=6; S7 No Abx, N=5.

FIG. 4A shows representative H&E sections of mouse lungs at 3 days follow-up after MHV-68 infection without antibiotic pre-treatment (top row) or after antibiotic pre-treatment (bottom row) and with saline, Serp-1 or S-7 treatment. Scale bar is 100 μm. FIG. 4B shows alveolar wall thickness and FIG. 4C alveolar lumen area of mouse lungs at 3 days follow-up as in FIG. 4A. FIG. 4D is a representative CD3 IHC micrographs of mouse lungs at 3 days follow-up after MHV-68 infection without antibiotic pre-treatment (top row) or after antibiotic pre-treatment (bottom row) and with saline, Serp-1 or S-7 treatment. Scale bar is 20 μm. FIGS. 4E-4G illustrate quantification of CD3+(FIG. 4E), CD4+(FIG. 4F), and CD8+ (FIG. 4G) cells per 40x field from 3-6 fields per mouse. Statistics in B, C and E performed by Two-Way ANOVA with Fisher's LSD post-hoc analysis. *p<0.05, p<0.01, *p<0.001; n.s. is not significant. N=3 for all conditions.

FIG. 5A shows representative IHC images of 100× fields depicting MHV-68 antigen staining in the lungs of mice at 3 days follow-up after MHV-68 infection without antibiotic pre-treatment (top row) or after antibiotic pre-treatment (bottom row) and with saline, Serp-1 or S-7 treatment. FIG. 5B shows quantification of percent of MHV-68 positively stained cells per 100x field from 3 fields per mouse. N=3 for all conditions.

DETAILED DESCRIPTION

Figure 1B:
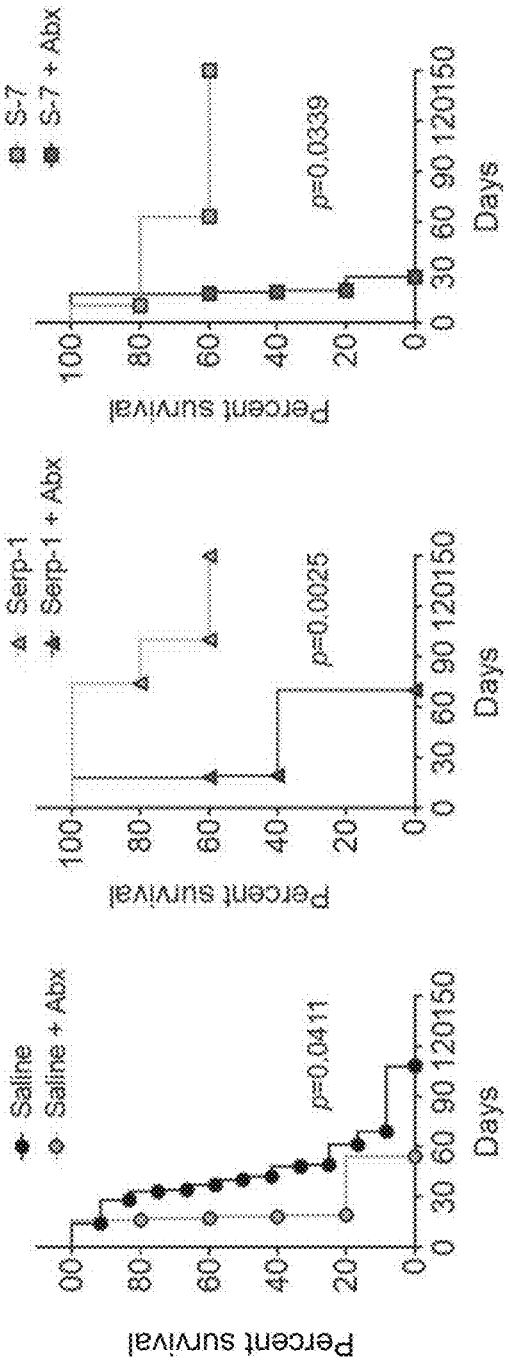
FIG. 1B is a Kaplan-Meier curve depicting survival of IFNγR$^{-/-}$ mice infected with MHV-68 and treated with saline (left; N=12 and 5), Serp-1 (middle; N=5 and 5), or S-7 (right; N=5 and 5) without or with antibiotics.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Abbreviations:
DIC: Disseminated intravascular coagulation
GHV: Gammaherpesvirus
MHV-68: Murine gammaherpesvirus-68
MYXV: Myxomavirus
IVS: Inflammatory vasculitic syndromes
GCA: Giant Cell Arteritis
TD: Takayasu's Disease
KD: Kawasaki Disease
RCL: Reactive center loop
IFNγ: Interferon gamma
TNFα: Tumor necrosis factor alpha
IFNγR: Interferon gamma receptor
IP: Intraperitoneal The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B. It is further to be understood that all base sizes and all molecular weight or molecular mass values given for nucleic acids are approximate and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. Unless otherwise defined, all technical terms used herein have the same meaning as commonly understood.

As used herein, "amplicon sequence variant" (ASV) is a term used to refer to individual DNA sequences recovered from a high-throughput marker gene analysis following the removal of spurious sequences generated during PCR amplification and sequencing. ASVs are thus inferred sequences of true biological origin. The term was introduced to distinguish between traditional methods that delineate operational taxonomic units (OTUs) generated by clustering sequences based on a shared similarity threshold and newer alternative methods that resolve individual sequences without clustering. Because ASV methods are able to resolve sequences that differ by as little as a single nucleotide and avoid similarity-based clustering, ASVs are also referred to as exact sequence variants (ESVs) or zero-radius OTUs (zOTUs)

As used herein, "clinical outcome" Refers to the health status of a patient following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, advanced or aggressive disease, disease recurrence, death, and favorable or poor response to therapy.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature. (See, for example, Remington, The Science and Practice of Pharmacy (latest edition)). In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include cytokine molecules (such as DNA or RNA) and proteins purified by standard purification methods. The term also embraces nucleic acid molecules and proteins prepared by recombinant expression in a host cell as well as chemically synthesized nucleic acid molecules and proteins.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, rodents (e.g., mice, rats, etc.) and the like. Preferably, the subject is a human patient. In particular embodiments, the subject of this disclosure is a human subject. A "subject in need thereof" or "a subject in need of" is a subject known to have, or is suspected of having a surface wound, such as a wound in the skin and surrounding tissue.

As used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

A "peptide" refers to any compound composed of amino acids or amino acid analogs chemically bound together. Peptide as used herein includes oligomers of amino acids, amino acid analog, or small and large peptides, including polypeptides or "proteins" refer to any chain of amino acids, regardless of length or post-translational modification (such as glycosylation or phosphorylation). In one example, a peptide is two or more amino acids joined by a peptide bond. Typically, a peptide consists of fewer than fifty amino acids; for example, consisting of approximately 7 to approximately 40 amino acids, consisting of approximately 7 to approximately 30 amino acids, consisting of approximately 7 to approximately 20 amino acids. In one example, a peptide consists of 4 amino acids and is referred to as a tetrapeptide.

"Peptide" applies to amino acid polymers to naturally occurring amino acid polymers and non-naturally occurring amino acid polymer as well as in which one or more amino acid residue is a non-natural amino acid, for example an artificial chemical mimetic of a corresponding naturally occurring amino acid.

A "polypeptide" is a polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide. The term "soluble" refers to a form of a polypeptide that is not inserted into a cell membrane.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitution |
| --- | --- |
| Ala | Syr |
| Arg | Lys |
| Asn | Gin, His |
| Asp | Glu |
| Cys | Ser |
| Gin | Asn |
| Glu | Asp |
| His | Asn, Gin |
| Ile | Leu, Val |
| Leu | He, Val |
| Lys | Arg, Gin, Glu |
| Met | Leu, He |
| Phe | Met, Leu, Tyr |
| Ser | Thr |
| Thr | Ser |
| Trp | Tyr |
| Tyr | Trp, Phe |
| Val | He, Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Although methods and materials similar or equivalent to those described herein can be used in the practice or testing of the present disclosure, suitable methods and materials are described below. All publications, patent applications, patents, and other references mentioned herein are incorporated by reference in their entirety. Unless otherwise defined, all technical terms used herein have the same meaning as commonly understood. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999. In addition, the materials, methods, and examples are illustrative only and not intended to be limiting.

Compositions and Methods of Use

Serine protease inhibitors, or serpins, are ubiquitous, complex, and highly active regulatory molecules that effectively control multiple coagulation, inflammatory, and neuroendocrine pathways. Serp-1 is a secreted myxomavirus-derived, purified protein that binds and inhibits urokinase- and tissue-type plasminogen activators (uPA and tPA, respectively), piasmin, factor X (fXa) and thrombin (in the presence of heparin at defined concentrations).

As disclosed herein the inventors have discovered that compositions including Serp-1 polypeptides, for example full length Serp-1 polypeptide or biologically active fragments thereof improve survival in vasculitis, such as MHV-68 lethal vasculitis. In particular, Serp-1 and Serp-1 RCL-derived peptide S-7 has been demonstrated to improve survival in MHV-68 vasculitis. Further, gut microbiome ablation accelerates MHV-68 lethality and abrogates Serp-1 and S-7 effectiveness. Moreover, the effect of microbiome ablation on early MHV-68 induced lung pathology is demonstrated. The effect of MHV-68 and Serp-1 or S-7 on microbiome composition is also provided.

Disclosed herein are formulations that include Serp-1 polypeptides and/or biologically active fragments and derivatives thereof, for example, Serp-1 polypeptides and fragments, such as Serp-1 RCL-derived peptide S-7, that improve survival, decrease, reduce, prevent and/or inhibit one or more signs or symptoms associated with vasculitis in a mammalian subject topically administered a Serp-1 polypeptide or a fragment thereof. In one embodiment, a Serp-1 polypeptide comprises the amino acid available at GENBANK accession no. NP_051722 and having the amino acid sequence set forth as:

MKYLVLVLCL TSCACRDIGL VVTFRYVYNES DNWFSPYGL TSALSVLRIA AGGNTKREID VPESWEDSD AFLALRELFV DASVPLRPEF TAEFSSRFNT SVQRVTFNSE NVKDVINSYV KDKTGGDVPR VLDASLDRDT KMLLLSSVRM KTSWRHVFDP SFTTDQPFYS GNVTYKVRMM NKIDTLKTET FTLRNVGYSV TELPYKRRQT AMLLWPDDL GEIVRALDLS LVRFWIRNMR KDVCQVVMPK FSVESVLDLR DALQRLGVRD AFDPSRADFG QASPSNDLYV TKVLQTSKIE ADERGTTASS DTAITLIPRN ALTAIVANKP FMFLIYHKPT TTVLFMGTIT (SEQ ID NO: 1)

Serp-1 polypeptides includes polypeptides having at least 80%, such as at least 81%, at least 82%, at least 83%, at least 84%, at least 85%, at least 86%, at least 87%, at least 88%, or at least 89% at least 90%, at least 91%, at least 92%, at least 93%, at least 94%, at least 95%, at least 96%, at least 97%, at least 98%, at least 99% or even 100% sequence identity to the amino acid sequence set forth as SEQ ID NO: 1 as well as biologically active fragments thereof. In embodiments, a Serp-1 polypeptide includes a Serp-1 reactive center loop-derived peptide or a series of modified RCL peptides. In some embodiments, Serp-1 reactive center loop-derived peptide has an amino acid at least 95%, at least 96%, at least 97%, at least 98%, at least 99% or even 100% sequence identity to the amino acid sequence set forth as GTTASSDTAITLIPR (SEQ ID NO: 2).

The disclosed isolated peptides include synthetic embodiments of peptides described herein. In addition, analogs (non-peptide organic molecules), derivatives (chemically functionalized peptide molecules obtained starting with the disclosed peptide sequences) and variants (homologs) of these peptides can be utilized in the compositions and methods described herein. Each peptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. In another example, carboxylic acid groups of the protein, whether carboxyl-terminal or side chain, can be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to C1-C16 alkyl or dialkyl amino or further converted to an amide.

Hydroxyl groups of the peptide side chains may be converted to C1-C16 alkoxy or to a C1-C16 ester using well-recognized techniques. Phenyl and phenolic rings of the peptide side chains may be substituted with one or more halogen atoms, such as fluorine, chlorine, bromine or iodine, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides to select and provide conformational constraints to the structure that result in enhanced stability. While the peptides of the present disclosure can be linear or cyclic, cyclic peptides generally have an advantage over linear peptides in that their cyclic structure is more rigid and hence their biological activity can be higher than that of the corresponding linear peptide. Any method for cyclizing peptides can be applied to the serpin-derived peptides or fragments described herein.

As noted, the Serp-1 polypeptides can vary in length and can be or can include contiguous amino acid residues that naturally occur in Serp-1 or that vary to a certain degree from a naturally occurring Serp-1 sequence (but retain a biological activity). Where the fragments include, at their N-terminus or C-terminus (or both), amino acid residues that are not naturally found in Serp-1 the additional sequence(s)

can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 20 150, 160, 170, 180, 190, or 200 residues, and one terminus can include none (e.g., it can terminate in an amino acid sequence identical to a naturally occurring Serp-1 sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues. Where biologically active variants of a Serp-1 fragment are used, the variant can vary by substitution of one or more amino acid residues within these groups. The variants can include a conservative amino acid substitution.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a peptide having measurable Serp-1 activity. For computer modeling applications, a pharmacophore is an idealized three-dimensional definition of the structural requirements for biological activity. Peptido- and organomimetics can be designed to fit each pharmacophore with current computer modeling software.

In embodiments, a Serp-1 polypeptide is included in a fusion protein. Thus, the fusion protein can include a Serp-1 polypeptide and a second heterologous moiety, such as a myc protein, an enzyme or a carrier (such as a hepatitis carrier protein or bovine serum albumin) covalently linked to the Serp-1 polypeptide. A second heterologous moiety can be covalently or non-covalently linked to the Serp-1 polypeptide. The Serp-1 polypeptide can be included in a fusion protein and can also include heterologous sequences.

Nucleic acids encoding one or more Serp-1 polypeptide are envisioned. These polynucleotides include DNA, cDNA and RNA sequences which encode the peptide(s) of interest. Nucleic acid molecules encoding these peptides can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same peptide.

Nucleic acid sequences encoding one or more Serp-1 polypeptide can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68: 109-151, 1979; the diethylphosphoramidite method of Beaucage et al., Tetra. Lett. 22: 1859-1862, 1981 the solid phase phosphoramidite triester method described by Beaucage & Caruthers, Tetra. Letts. 22(20): 1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding one or more Serp-1 polypeptide disclosed herein can be prepared by cloning techniques or chemical synthesis. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (San Diego, CA), and Applied Biosystems (Foster City, CA), as well as many other commercial sources known to one of skill.

Once the nucleic acids encoding one or more Serp-1 polypeptide are isolated and cloned, the peptide can be expressed in a recombinantly engineered cell such as bacteria, plant, yeast, insect and mammalian cells using a suitable expression vector or expressed in a viral vector for therapeutic approaches—e.g., Adeno-associated viral (AAV) vector expression. One or more DNA sequences encoding one or more immunogenic peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. In one example, a vector is an AAV vectror.

Polynucleotide sequences encoding one or more Serp-1 polypeptide can be operatively linked to expression control sequences (e.g., a promoter). An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding one or more Serp-1 polypeptide can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

In an aspect, a composition disclosed herein comprises nucleic acid molecules that encode the serpin-derived peptides or fragments thereof disclosed herein in an expression construct or in a single or separate cassette. Disclosed herein is an expression construct capable of expressing serpin-derived peptides or fragments thereof.

A disclosed expression cassette can include 5' and 3' regulatory sequences operably linked to a polynucleotide disclosed herein. "Operably linked" is intended to mean a functional linkage between two or more elements. For example, an operable linkage between a polynucleotide disclosed herein and a regulatory sequence (e.g., a promoter) is a functional link that allows for expression of a polynucleotide disclosed herein. Operably linked elements can be contiguous or non-contiguous. When used to refer to the joining of two protein coding regions, by operably linked is intended that the coding regions are in the same reading frame. An expression cassette may further comprise at least one additional polynucleotide to be co-transformed into the organism. Alternatively, one or more polypeptide(s) can be expressed on one or more expression cassettes. Expression cassettes can be provided with a plurality of restriction sites and/or recombination sites for insertion of the polynucleotide to be under the transcriptional regulation of the regulatory regions.

The regulatory regions (i.e., promoters, transcriptional regulatory regions, and translational termination regions) and/or the polynucleotides disclosed herein can be native/analogous to the host cell or to each other. Alternatively, the regulatory regions and/or the polynucleotide employed in the invention can be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction, annealing, resubstitutions, e.g., transitions and transversions, can be involved, A number of promoters can be used in the practice of the invention. The promoters can be selected based on the desired outcome. The choice of promoters depends on several factors including but not limited to efficiency, selectability, inducibility, desired expression level, and cell- or tissue-preferential expression. The nucleic acids can be combined with constitutive, tissue-preferred, inducible, or other promoters for expression in the host organism. One skilled in the art is capable of appropriately selecting and positioning promoters and other regulator}' regions relative to the coding sequence.

In addition to Serp-1 polypeptide and/or nucleic acids encoding the Serp-1 polypeptides, the formulation can further include one or more carriers, excipients, and additional active agents. The dosage and administration regimen for the described methods will depend on the nature and condition, such as the nature and condition of the vasculitis. The subject to be treated by the formulation can be a human or a non-human mammal.

In embodiments, methods are provided for preventing, treating, reducing and/or inhibiting one or more disorders in a subject, such as a virus and/or inflammatory disorder, thereby improving the survival of the subject. In some embodiments, methods are provided for treating, preventing, inhibiting and/or reducing herpesvirus infections, such as gammaherpesviruses (GHV), including MHV-68. In some embodiments, methods are provided for treating, preventing, inhibiting and/or reducing one or more signs and/or symptoms associated with an inflammatory vasculitic syndrome.

In embodiments, the methods include administering to the subject an effective amount of a composition that includes one or more peptides disclosed herein. In some embodiments, the methods include administering to the subject an effective amount of a composition that includes one or more of Serp-1 and Serp-1 RCL-derived peptide S-7. In some embodiments, methods of using the disclosed peptides to treat other disorders, such as juvenile rheumatoid arthritis, polymyalgia rheumatic, reactive arthritis, relapsing polychrondritis, polymyositis, undifferentiated connective tissue disease, dermatomyositis, dermatitis herpetiformis, Celiac disease, inflammatory bowel disease, ulcerative colitis, Crohn's disease, uveitis, macular degeneration, dry eyes, systemic lupus erythematosus with or without diffuse alveolar hemorrhage, pulmonary hypertension, sarcoidosis, glomerulonephritis, diabetes, transplant vasculopathy, portal hypertension, Takayasu's disease, Giant Cell Arteritis, Kawasaki Disease, polyeratitis nodosa, Behcet's disease, Raynaud's disease, Chagas disease, myocarditis, post-infarction disease, inflammatory cardiomyopathy, and Buerger's disease (thromboangiitis obliterans) are provided. The disclosed peptides can be used alone or in combination therapy with other compositions or drugs used to treat the foregoing conditions. Such combination therapies include, but are not limited to, simultaneous or sequential administration of the drugs used for preventing, treating, inhibiting and/or reducing the disorder, such as GHV and/or an inflammatory vasculitic syndrome. These additional therapies would not include antibiotics or other compositions that destroy microbiota that are associated with protecting the gut bacterial microbiome, such as ASV4, or increase microbiota, or increase microbiota associated with a patho-exacerbative phenotype such as ASV1 and ASV123.

In some embodiments, the methods include administering an effective amount of a composition with one or more disclosed peptides instead of antibiotics in a subject that has acquired or is at risk of acquiring herpesvirus infections, such as gammaherpesviruses (GHV), including MHV-68, or an inflammatory vasculitic syndrome.

In some embodiments, the method includes selecting a subject having or at risk of acquiring herpesvirus infections, such as gammaherpesviruses (GHV), including MHV-68, or at risk for developing an inflammatory vasculitic syndrome or a range of auto-immune and auto-inflammatory disorders. In some embodiments, selecting a subject having or at risk of acquiring herpesvirus infections, such as gammaherpesviruses (GHV), including MuHV4/MHV-68, HHV4/EBV, HHV8/KSHV or an inflammatory vasculitic syndrome includes characterizing a subject's gut microbiome, wherein the presence of ASV4 indicates the subject as a candidate for treatment with one or more of the disclosed compositions.

The disclosed peptides can be administered by any means known to one of skill in the art, such as by systemic, intramuscular, subcutaneous, intraperitoneal, intravenous, oral, nasal, or anal administration is contemplated. In one embodiment, administration is by subcutaneous or intramuscular injection. To extend the time during which the peptide is available to inhibit or treat the disorder, the peptide can be provided as an implant, an oily injection, or as a particulate system. The particulate system can be a microparticle, a microcapsule, a microsphere, a nanocapsule, or similar particle (Banga, "Parenteral Controlled Delivery of Therapeutic Peptides and Proteins," in Therapeutic Peptides and Proteins, Technomic Publishing Co., Inc., Lancaster, PA, 1995).

In some examples, the provided peptides are combined with a pharmaceutically acceptable carrier (e.g., a phospholipid or other type of lipid) or vehicle for administration to human or animal subjects. In some embodiments, more than one disclosed peptide can be combined to form a single preparation. The peptides can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostatic agents, and/or solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art including, but not limited to 0.9% normal saline, or Citrate-buffered saline (CBS), or Phosphate-buffered saline (PBS), or Ringer's Lactate solution (RL), or Acetated Ringer's solution (AR), or 5% or 10% dextrose in normal saline (D5NS, D10NS), or 5% or 10% dextrose in half-normal saline (D5HNS, D10HNS), or Hank's balanced salt solution (HBSS), or Earle's balanced salt solution (EBSS), or Gey's balanced salt solution (GBSS), or TRIS-buffered saline (TBS), or HEPES-buffered saline (HBS).

The pharmaceutical compositions provided herein may be administered through different routes, such as systemic, oral, including buccal and sublingual, rectal, parenteral, aerosol, nasal, intramuscular, intraperitoneal, subcutaneous, intradermal, and topical. They may be administered in different forms, including but not limited to solutions, emulsions and suspensions, microspheres, particles, microparticles, nanoparticles, and liposomes.

In embodiments, administration can be by direct injection at the site (or former site) of a tissue that is to be treated. In another embodiment, the pharmaceutical compositions are delivered in a vesicle, in particular liposomes (see, e.g., Langer, Science 249:1527-1533, 1990; Treat et al., in Liposomes in the Therapy of Infectious Disease and Cancer, Lopez Berestein and Fidler (eds.), Liss, N.Y., pp. 353 365, 1989). In one embodiment, administration is by IP injection over the course of days. In another embodiment the agent can be delivered by a viral vector such as AAV or lentivirus).

In embodiments, the pharmaceutical compositions can be delivered in a controlled release system. In one embodiment, a pump can be used (see, e.g., Langer Science 249:1527-1533, 1990; Sefton Crit. Rev. Biomed. Eng. 14:201-240, 1987; Buchwald et al., Surgery 88:507-516, 1980; Saudek et al., N. Engl. J. Med. 321:574-579, 1989). In another embodiment, polymeric materials can be used (see, e.g., Ranger et al., Macromol. Sci. Rev. Macromol. Chem. 23:61-64, 1983; Levy et al., Science 228:190-192, 1985; During et al., Ann. Neurol. 25:351-356, 1989; and Howard et al., J. Neurosurg. 71:105-112, 1989). Other controlled release systems, such as those discussed in the review by Langer (Science 249:1527-1533, 1990), can also be used.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. An example of such a dosage range is 10 ng/kg up to 0.001 to 200 mg/kg body weight in single or divided doses. Another example of a dosage range is 1.0 µg to 100 mg/kg body weight in single or divided doses.

In some examples, an effective amount of a disclosed pharmaceutical composition is one in which one or more signs or symptoms associated with a virus and/or inflammatory disorder is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the composition. For example, an effective amount of a disclosed pharmaceutical composition is one in which one or more signs or symptoms associated with herpesvirus infections, such as gammaherpesviruses (GHV), including MHV-68, is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the composition. In one example, an effective amount of a disclosed pharmaceutical composition is one in which one or more signs or symptoms associated with an inflammatory vasculitic syndrome is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the composition.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration.

Single or multiple administrations of the composition comprising one or more of the disclosed conjugates can be carried out with dose levels and pattern being selected by the treating physician. Generally, multiple doses are administered.

In a particular example, the composition is administered by IV, IM, SC or IP once per day or by an infusion pump continuously. It is contemplated that the composition can be administered daily, every other day, twice a week, weekly, or monthly. Treatment will typically continue for at least a month, more often for two or three months, sometimes for six months or a year, and may even continue indefinitely, i.e., chronically. Repeat courses of treatment are also possible.

In one embodiment, administration is by IP injection such as from about 1 ng/kg to about 100 µg/kg, including a 100 ng/g dose over a course of days, such as for at least one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks or more, such as one month, two months, three months, four months, five months, six months, seven months, eight months, nine months, ten months, eleven months, twelve months. By way of example, intramuscular injections may range from about 0.5 ml to about 3 ml. In some other examples, the method is by IV.

Kits

Provided by this disclosure are kits that can be used to prevent, treat, reduce or inhibit one or more disorders in a subject, such as a virus and/or inflammatory disorder, thereby improving the survival of the subject. In some embodiments, a kit is disclosed herein for treating, preventing, inhibiting and/or reducing herpesvirus infections, such as gammaherpesviruses (GHV), including MHV-68. In some embodiments, kits are provided for treating, preventing, inhibiting and/or reducing one or more signs and/or symptoms associated with an inflammatory vasculitic syndrome. Exemplary kits include at least one of the disclosed pharmaceutical compositions. The disclosed kits can include instructional materials disclosing means of use of the compositions in the kit. The instructional materials can be written, in an electronic form (such as a computer diskette or compact disk) or can be visual (such as video files).

The following examples are provided to illustrate particular features of certain embodiments. However, the particular features described below should not be construed as limitations on the scope of the disclosure, but rather as examples from which equivalents will be recognized by those of ordinary skill in the art.

Example

Immune modulating proteins from myxomavirus (MYXV) provide a new class of anti-inflammatory treatments when delivered as recombinant protein or by ectopic expression after Adeno-associated virus (AAV) delivery. MYXV is the causative agent of lethal myxomatosis in the European rabbit (Oryctolagus *cuniculus*), expressing highly potent immune evasion proteins that act as virulence factors in MYXV infections. MYXV is not a pathogen for mice or humans. When purified as isolated recombinant proteins, these immune modulating biologics can modify disease progression in a wide range of inflammatory diseases in preclinical animals and man. The MYXV-derived serine protease inhibitor (serpin) Serp-1 and a Serp-1 reactive center loop (RCL) peptide S-7 ($G_{305}$TTASSD-TAITLIPR$_{319}$— SEQ ID NO:2) significantly improved survival, reducing pulmonary and aortic inflammation as well as hemorrhagic lung consolidation after MHV-68 infection. Serp-1 targets the coagulation pathways, both thrombolytic and thrombotic, and has proven, highly effective anti-inflammatory functions. Antibiotic treatment of IFNγR$^{-/-}$ mice prior to MHV-68 infection abrogated the efficacy of S-7 treatment for lethal MHV-68 infections, leading to significantly reduced survival. These modified peptides are very important.

Therapeutically modified S-7 peptides (MPS7-8, GTTASSDTAITLEPR, (SEQ ID NO: 5) and MPS7-9, GTTASSDTAITDEPR (SEQ ID NO: 6)), designed based upon the serpin crystal structure, maintained efficacy in this model with improved survival after MHV-68 infection. The MPS7 peptides have predicted increased hydrogen bonds when compared to the native S-7 peptide (Mahon et al., Biochemistry, 57, 1096-1107 (2018)).

The pathophysiologic role of the gut bacterial microbiome in gammaherpesviral infections and on immune modulating treatments has not previously been investigated. In this Example, a systematic examination of the role of the gut bacterial microbiome in MHV-68 infection and on Serp-1 and Serp-1-derived S-7 peptide treatment in MHV-68 infections is investigated.

Methods

Animals. IFNγR$^{-/-}$ mice (B6.129S7-Ifngr1$^{tm1Agt}$/J) were purchased from the Jackson Laboratory (Bar Harbor, ME, USA). Animals were housed in barrier conditions at the University of Florida Animal Care Services vivarium and bred under specific pathogen-free conditions. Mice were weaned at 3 weeks, maintained on a 12-hour light-dark cycle and were fed water and standard rodent chow ad libitum.

Antibiotic treatment. At 4 weeks of age, IFNγR$^{-/-}$ mouse cohorts were transferred from the ABSL1 colony to a separate, ABSL2 colony. Gut microbiome suppression was achieved by replacing standard drinking water with autoclaved reverse osmosis water (obtained from the same animal care facility) containing an antibiotic cocktail (Table 1) composed of Streptomycin (2 g/L), Gentamicin (0.5 g/L), Bacitracin (1 g/L) and Ciprofloxacin (0.125 g/L) for 10 days. One day (24 hours) prior to infection, medicated water was replaced with standard animal care facility water, which was maintained for the remainder of the experiment.

TABLE 1

Antibiotic cocktail components

| Antibiotic | Dose | Target class | Mechanism of action |
|---|---|---|---|
| Bacitracin | 1 g/L | Gram-positive | Cell wall synthesis inhibition[82] |
| Gentamicin | 0.5 g/L | Gram-negative and Gram-positive | Ribosome inhibition[83] |
| Streptomycin | 2 g/L | Gram-negative and Gram-positive | Ribosome inhibition[84] |
| Ciprofloxacin | 0.125 g/L | Gram-negative and Gram-positive | DNA replication inhibition[85] |

MHV-68 infection. On day 11 (after 10 days of antibiotics) mice (5 weeks old) were infected with MHV-68 at a dose of 12.5×106 PFU in 0.1 mL DMEM by intraperitoneal (IP) injection as previously described22,25,27,30. Mice were returned to the colony and monitored for signs of distress for the duration of the experiment. Mice were either followed for 150 days to determine survival or euthanized at 3 days post-infection and organs harvested into formalin for histology or RNAlater (Thermo Scientific, USA) for microbiome analyses. Details on the numbers of MHV-68-infected mice in this study are detailed in Table 2.

TABLE 2

MHV-68-infected mice (total of 73 mice)

| Treatment | Antibiotics (ABX) | Follow-up | # of mice |
|---|---|---|---|
| Saline | No | 3 days | 6 |
|  | Yes | 3 days | 6 |
|  | No | 150 days | 12 |
|  | Yes | 150 days | 5 |
| Serp-1 | No | 3 days | 6 |
|  | Yes | 3 days | 6 |
|  | No | 150 days | 5 |
|  | Yes | 150 days | 5 |
| S-7 | No | 3 days | 6 |
|  | Yes | 3 days | 6 |
|  | No | 150 days | 5 |
|  | Yes | 150 days | 5 |

Gut bacterial microbiome sample processing. Large intestine samples preserved in RNAlater were processed for total genomic DNA isolation using the ZymoBiomics® miniprep kit (Zymo Research) according to manufacturer's recommended procedure. Isolated DNA was quantified using a NanoDrop 2000C (Thermo Scientific) and stored at −80° C. Samples were analyzed in the Arizona State University KED Genomics Core for whole-sample 16S rRNA gene amplicon sequencing. DNA library preparation for Illumina® MiSeq platform was prepared according to the protocol from Earth Microbiome Project (world wide web address—earthmicrobiome.org/emp-standard-protocols/16s). The 16S primer set 515f-806r 86 was used for 2×150 pair-ended sequencing.

Figure 4A:
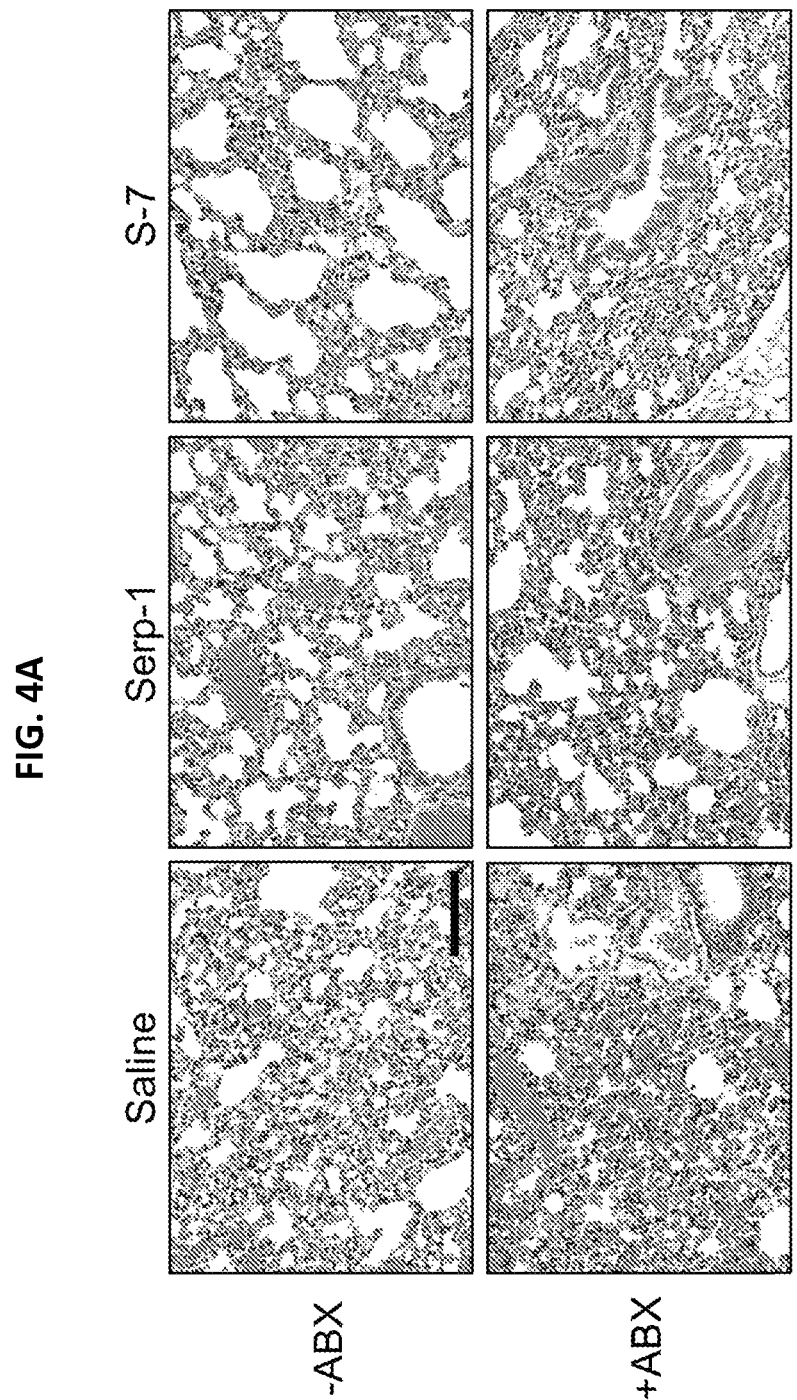
FIGS. 4A-4G illustrate microbiome-dependent Serp-1 and S-7 efficacy is associated with pulmonary inflammation and increased occupancy of CD3+ and CD8+ cells.
Figure 4B:
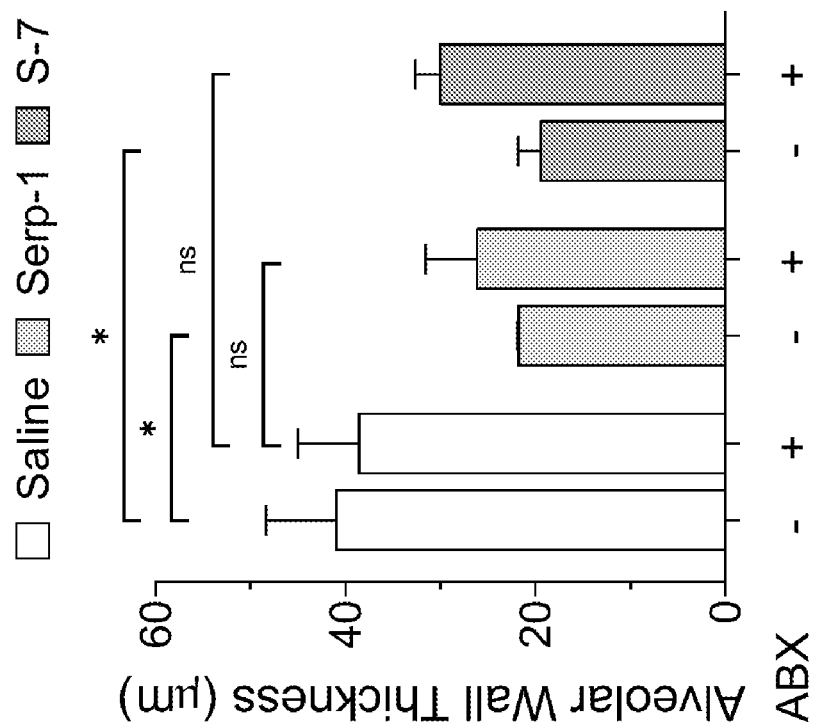
Figure 4C:
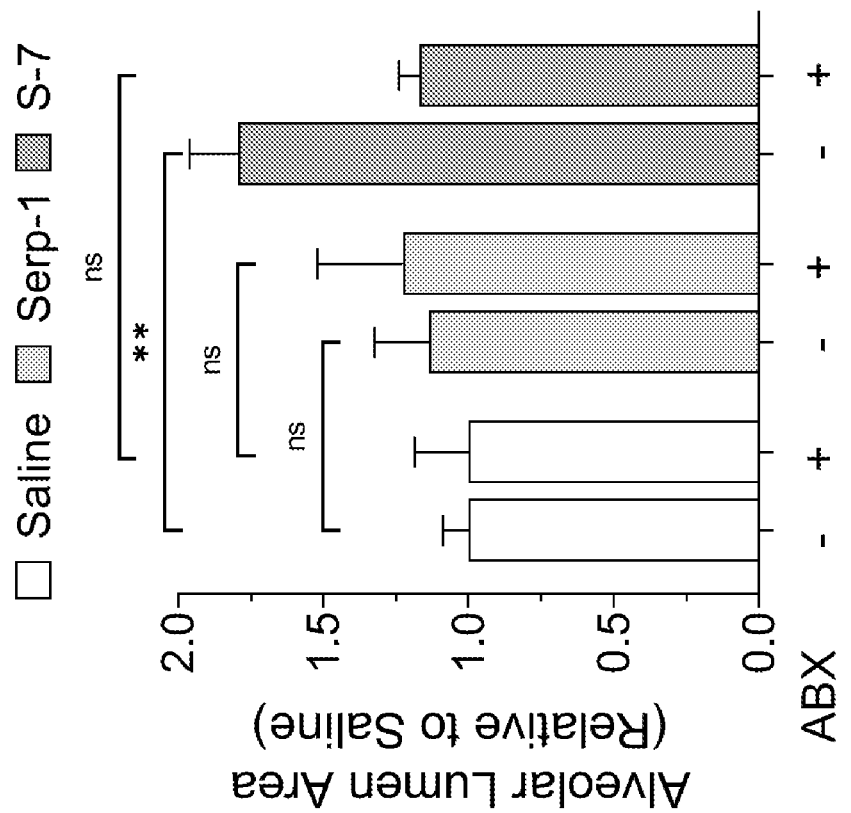
Figure 4D:
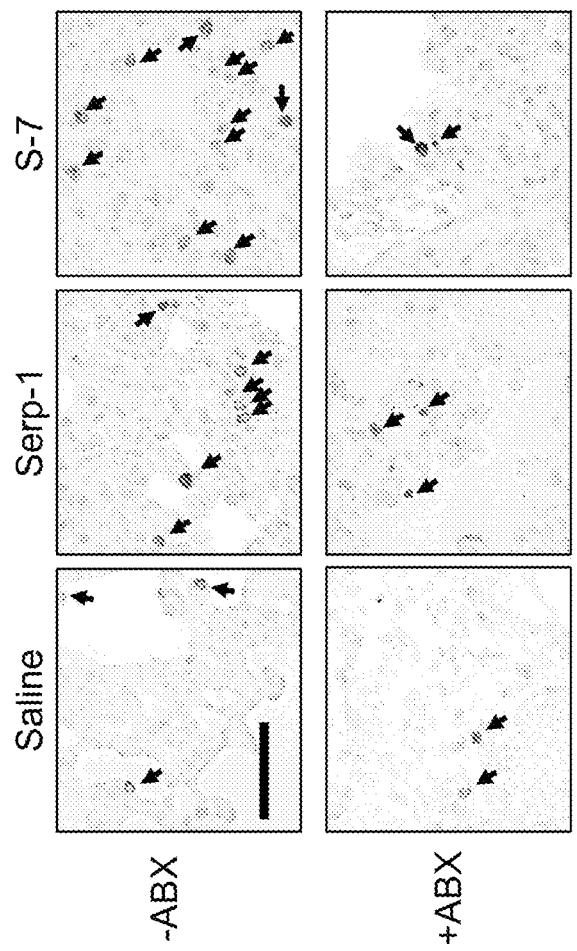
Figure 4E:
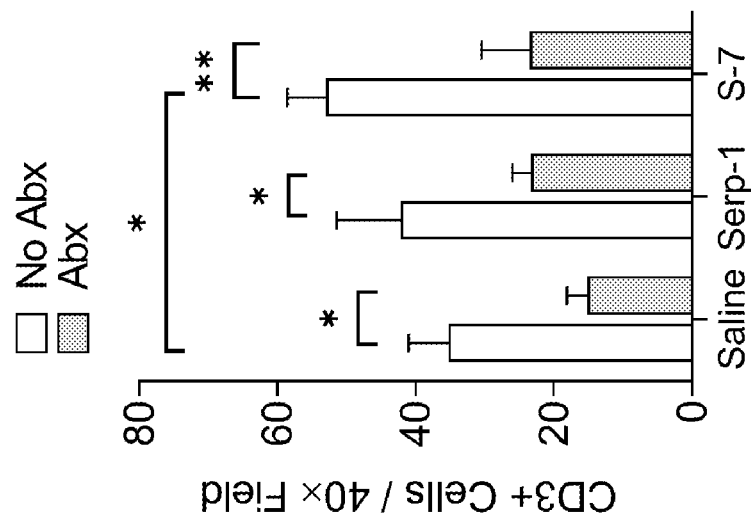
Figure 4F:
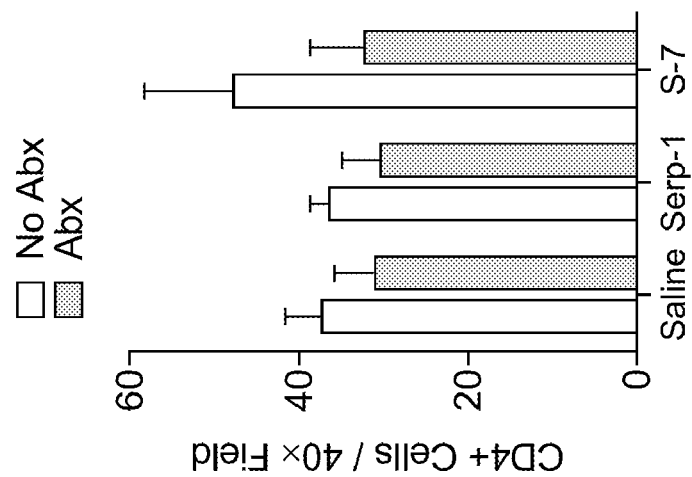
Figure 7:
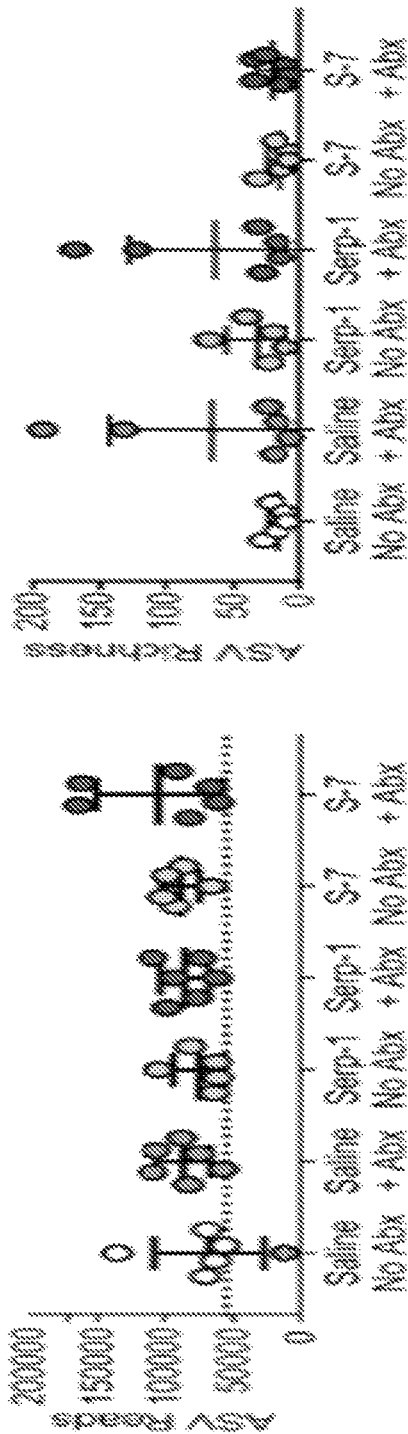
FIG. 7A shows ASV reads of each sample is shown. One saline no abx sample was omitted for low reads (12,107 reads), as labeled in gray. There was no statistically significant difference between the groups as assessed by Mann-Whitney test.
FIG. 7B shows richness (number of observed bacterial ASV) is plotted (n=33).
FIG. 7C shows results of differential analyses by likelihood test, DeSeq2 and LefSe between saline no abx mice and Serp-1 no abx mice are shown.
FIG. 7D shows results of differential analyses by likelihood test, DeSeq2 and LefSe between saline no abx mice and S7 no abx mice are shown.
FIG. 7E shows results of differential analyses by likelihood test, DeSeq2 and LefSe between Saline no abx mice and combined Serp1/S7 no abx mice are shown. As illustrated in 7C-7E, ASV identified as significantly different in their respective analyses are indicated by "x", ASV not significantly different are indicated by "–".

16S rRNA gene amplicon sequencing and analysis. Illumina MiSeq sequencing reads (2×150 bp) of the 16S rRNA gene V4 region 87 were analyzed with QIIME 2 (ver 2017.12)88 for 34 samples: Saline+Abx (n=6), Saline No Abx (n=6), Serp-1+Abx (n=6), Serp-1 No Abx (n=5), S7+Abx (n=6), S7 No Abx (n=5). Sequencing reads were processed with DADA2 to infer Amplicon Sequence Variants (ASVs) at a 97% identity threshold using Greengenes database (version 13.8)89. To account for inter-sample depth variability, all samples were rarefied to 55,000 reads per sample (10 iterations) (FIGS. 7A-7B). One sample (12,107 reads; Saline No Abx group) was omitted due to insufficient reads and the remaining 33 samples were preserved for further analysis. ASV richness, alpha diversity (Shannon's Diversity Index) and beta diversity (UniFrac distance) were calculated using QIIME 2. Statistical analyses (read depth, ASV richness and Shannon Index comparisons) were performed with Mann-Whitney test. PCoA was performed with weighted unifrac distance in QIIME 2. To identify discriminating ASVs associated with the respective treatments, LEfSe (Linear discriminant analysis Effect Size), DESeq2 (version 1.20.0) and likelihood ratio tests were performed in R studio (Version 1.1.456) (FIGS. 7C-7E). Discriminating analyses were first performed compared Serp-1 (no Abx) to saline (no Abx) mice, S-7 (no Abx) to saline (no Abx) mice, and finally as a combined group of Serpin-treated mice [Serp-1 (no Abx) and S-7 (no Abx)] to saline (no Abx mice). Discriminant ASVs identified in these analyses were pooled and validated in heatmap and abundance analyses (FIGS. 4D-4F). Total 16S sequence data for these samples have been deposited to the NCBI Sequence Read Archive under BioProject accession number PRJNA517927.

Histopathology. Mice were euthanized at 3 days follow-up after infection by carbon dioxide asphyxiation followed by cervical dislocation. Organs were harvested and fixed in 10% neutral buffered formalin. Samples were dehydrated through graded alcohol, paraffin-embedded, sectioned into 4-6 µm ribbons, captured on charged glass and dried overnight at 37° C. prior to processing for histopathology. Slides were rehydrated, stained with Gill's hematoxylin No. 3 and Eosin Y (H&E) according to standard procedure, dehydrated and mounted in Cytoseal XYL (Thermo Fisher Scientific, USA).

Quantitative morphometry. H&E-stained aorta, lung and colon sections were imaged with a 20×/0.5NA objective on an Olympus BX51 microscope equipped with an Olympus DP74 camera operated by cellSens Dimensions v1.16 software. Objective-calibrated measurements of alveolar septal thickness and lumen area were collected using cellSens Dimensions. At least 50 measurements were collected and averaged for each mouse, and at least three mice were examined for each group. Images were processed for visualization in figures using ImageJ/FIJI v1.52i92.

Immunohistochemistry. FFPE blocks containing lung tissue were sectioned into 4-6 µm ribbons, captured on charged glass and dried overnight at 37° C. prior to processing. Slides were rehydrated and epitopes retrieved by boiling in sodium citrated buffer. Endogenous peroxidases were quenched with 3% hydrogen peroxide, slides were blocked in 5% bovine serum albumin in TBS/0.1% Tween 20 and sections were probed with rabbit polyclonal antibody against CD3 (Abcam ab5690; 1:200), CD4 (Abcam ab183685; 1:1000) or CD8 (Abcam ab209775; 1:2000). For MHV-68 detection, 1:500 rabbit anti-serum or pre-immune serum (as control) were used for immunostaining (kind gift of Dr. H. W. Virgin 1119). 1:500 goat anti-rabbit HRP was used for secondary staining (Jackson Immuno Research 111-035-144). Antigens were revealed with ImmPACT DAB (Vector Labs, USA) and mounted with Cytoseal XYL. Sections were imaged with a 40×/0.75NA objective.

Viral load determination by qPCR. Total DNA was isolated from each FFPE sample (4x5 µm thick sections for each sample was used) using the QIAamp DNA FFPE Tissue Kit according to the manufacturer's instructions. Samples were quantified using a DS-11 series spectrophotometer/fluorometer (Denovix, USA). Quantitative PCR (qPCR) was undertaken to investigate relative viral load using the following reaction per sample: 10 µL SsoAdvanced Universal SYBR Green Supermix (Bio-rad Laboratories Inc., USA), 0.4 μl each of the primers 65F (5'-GTCAGGGCC-CAGTCCGTA-3'; SEQ ID NO: 3) and 65R (5'-TGGCCCTCTACCTTCTGTTGA-3'; SEQ ID NO: 4), 200 ng of DNA and water up to 20 μL total volume. Reactions were run in triplicate with controls, and a standard curve using following cycling conditions used on a CFX96 (Bio-rad Laboratories, Inc., USA) instrument: 95° C. for 20 sec, 40 cycles (95° C. for 15 sec, 60° C. for 20 sec), followed by a melt curve analysis.

Statistical analysis. Survival and pathology statistics were analyzed with GraphPad Prism v8.0.1. Kaplan-Meier survival statistics were calculated using Log-rank (Mantel-Cox) testing. For visualization, individual comparison curves are presented. Lung pathology statistics were compared using a Two-Way ANOVA with a Fisher's LSD or Tukey's post-hoc test. Bars are mean±standard error. P-value less than 0.05 was considered significant. *p<0.05, p<0.01, *p<0.001, ****p<0.0001; n.s. is not significant.

Results

Serp-1 protein and S-7 peptide treatments improve survival after MHV-68 infection in IFNγR−/− mice MHV-68 infections establish chronic infection with latency in wildtype mice, causing only flu-like symptoms. Conversely, intraperitoneal infection of mice with underlying immune deficiency, as for IFNγR$^{-/-}$ mice, results in a lethal large vessel vasculitis, colitis and hemorrhagic pneumonia with early mortality. Intranasal infection, an alternative model for MHV-68, is not a model for severe vasculitic syndromes. This intraperitoneal infection model of vasculitis has been used to study the pathogenesis of gammaherpesvirus host-pathogen interactions, as well as to investigate the potential for anti-inflammatory treatment of associated inflammatory vasculitic syndromes. Intraperitoneal infection of IFNγR−/− mice with 12.5×106 pfu was performed with follow-up for 150 days to determine survival rates. MHV-68 infection with administration of control saline treatment alone for 30 days was lethal, with a median survival of 41 days. Serp-1 (100 ng/g) or S-7 (100 ng/g) IP injections for 30 days improved survival to 60% at 150 days (p=0.0022 and p=0.0218, respectively) (FIG. 1B). Thus, Serp-1 and S-7 protect IFNγR−/− mice after lethal MHV-68 infection.

Loss of gut bacteria accelerated MHV-68 induced disease

Figure 2A:
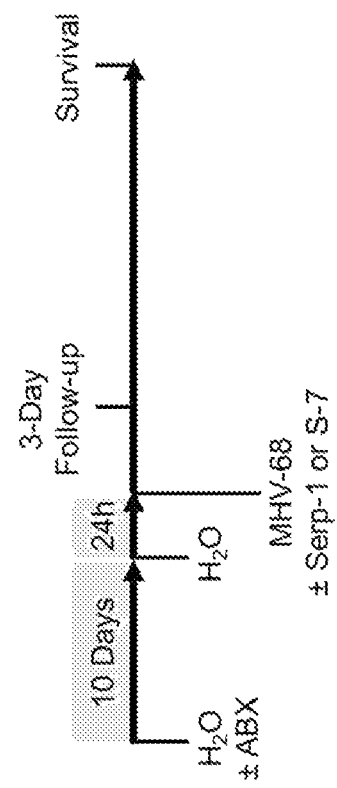

It was hypothesized that the gut bacterial microbiome may play a role in the host-pathogen interactions of MHV-68 induced disease through transkingdom interactions. A systematic analysis of the effect of microbiome depletion on MHV-68 induced disease progression was completed (FIG. 2A). Mice were maintained on medicated water containing a broad-spectrum cocktail of four antibiotics: bacitracin, gentamicin, streptomycin and ciprofloxacin (Table 1) in order to suppress gut bacterial populations. During this time the density of the gut bacteria (as measured by colony forming units [CFU] per gram fecal pellet) was markedly reduced, validating a decrease in bacterial load (FIG. 2B). After ten days, mice were returned to normal drinking water for 24 hours, during which time the antibiotic treatment maintained suppression of the microbiome (FIG. 2B). Mice were subsequently infected by IP injection of MHV-68 and injected with control saline daily for 30 days and survival assessed for up to 150 days.

Figure 2C:
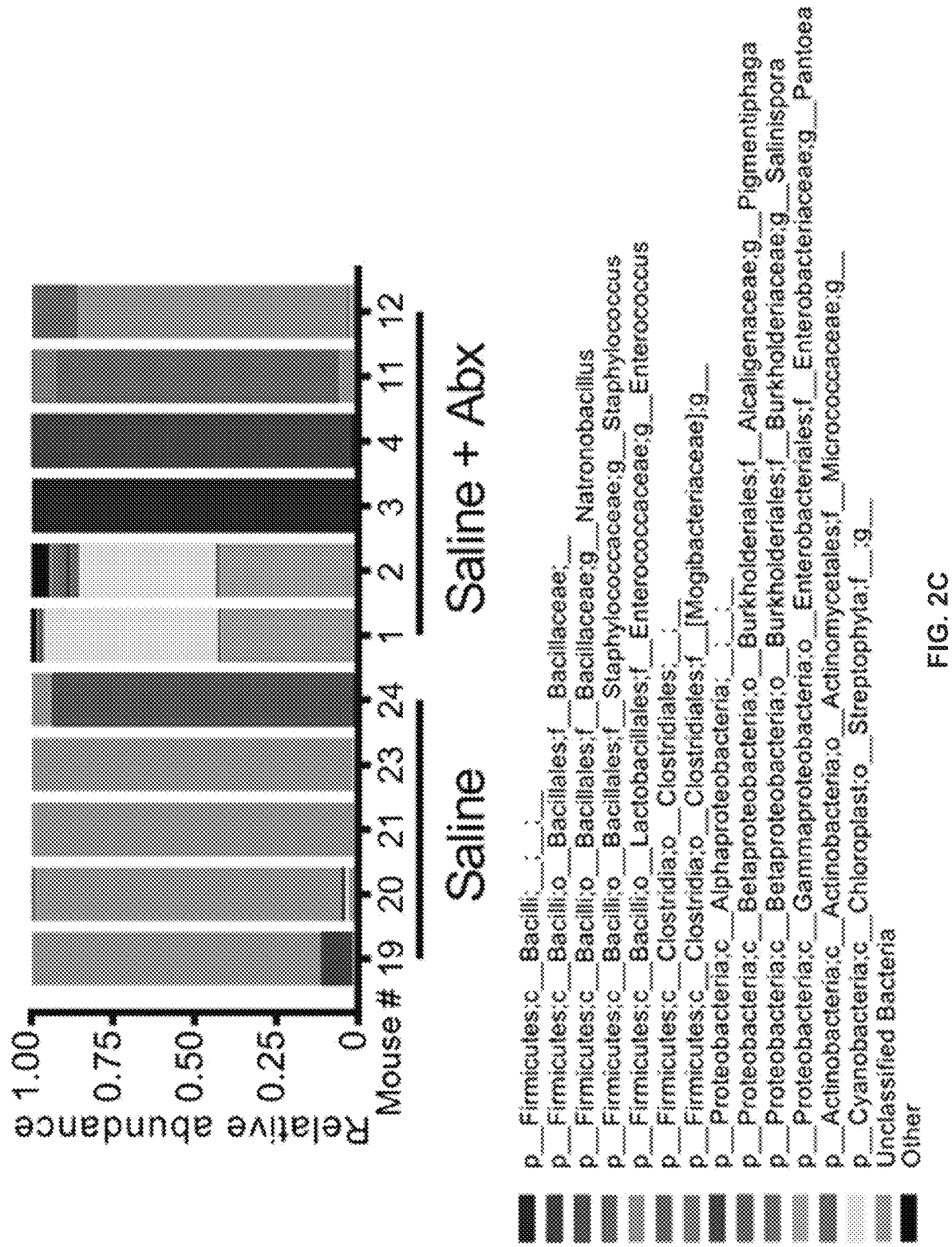
Figure 2D:
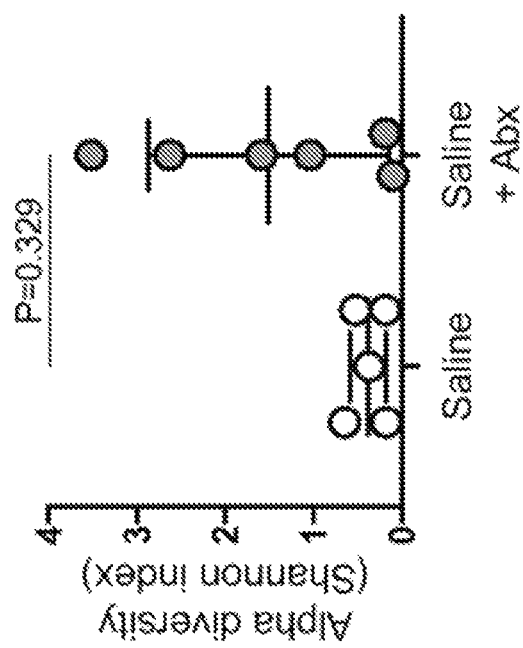
Figure 2E:
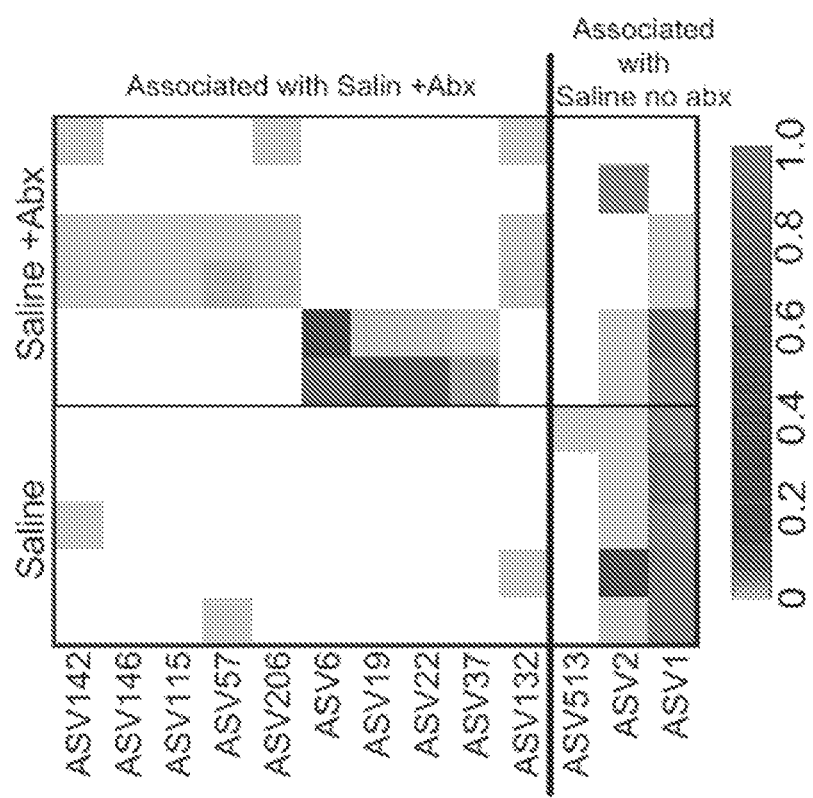

Suppression of gut bacteria by antibiotic treatment markedly accelerated the course of MHV-68 infection. Saline-treated mice exhibited a median survival of 41 days, while antibiotic-treated mice had a median survival of 19 days (p=0.0411; FIG. 1B). 16S rRNA gene amplicon sequencing was subsequently performed on DNA extracts from the large intestines of individual mice at 3 days post-MHV-68 infection in order to assess early changes in the gut microbiota. A distinct dysbiosis was detected in mice pre-treated with antibiotics prior to MHV-68 infection versus mice with a stable bacterial microbiome prior to infection (FIG. 2C). This dysbiosis was associated with a non-statistically significant trend towards increased diversity in ASV richness (FIG. 2D; p=0.329). Sub-population analysis revealed significant changes in candidate ASVs in MHV-68 infected mice that were associated with antibiotic treatment (FIG. 2E, top panels; increased abundance after antibiotics) or with no antibiotic treatment (FIG. 2E, bottom panels; decreased abundance after antibiotics). These results indicate that the gut bacterial microbiome is a significant determinant of MHV-68 induced disease progression.

Serp-1 and S-7 peptide treatment efficacy is dependent on the gut bacterial microbiota.

The potential for dependence of Serp-1 and S-7 therapeutic efficacy on the gut bacterial microbiome in MHV-68 infected IFNγR$^{-/-}$ mice was investigated. Mice were treated with medicated drinking water (Table 1) for 10 days, placed on normal water for 24 hours, then infected with MHV-68 and concurrently treated for 30 days with either Serp-1 or S-7 by IP injection. Mice were followed for survival or 3-day follow-up (FIG. 2A).

Serp-1 and S-7 peptide improved survival with 60% of mice surviving to 150 days after MHV-68 infection. In contrast, antibiotic-treated mice had accelerated disease, with a median survival of 19 (Serp-1; p=0.0025; FIG. 1B) and 18 days (S-7; p=0.0339; FIG. 1B). Serp-1 or S-7 efficacy after antibiotic treatment is not significantly different from saline treatment after antibiotics (Serp-1+Abx vs Saline+Abx, p=0.2012; S-7+Abx vs Saline+Abx, p=0.9164). Thus, the efficacy of Serp-1 or S-7 treatment and protection in lethal MHV-68 infections was dependent on the gut bacterial microbiome. The modified S-78 peptides again improved survival even with antibiotic treatments.

Microbiome analysis identifies candidate taxa associated with Serp-1 and S-7 treatments.

Figure 3A:
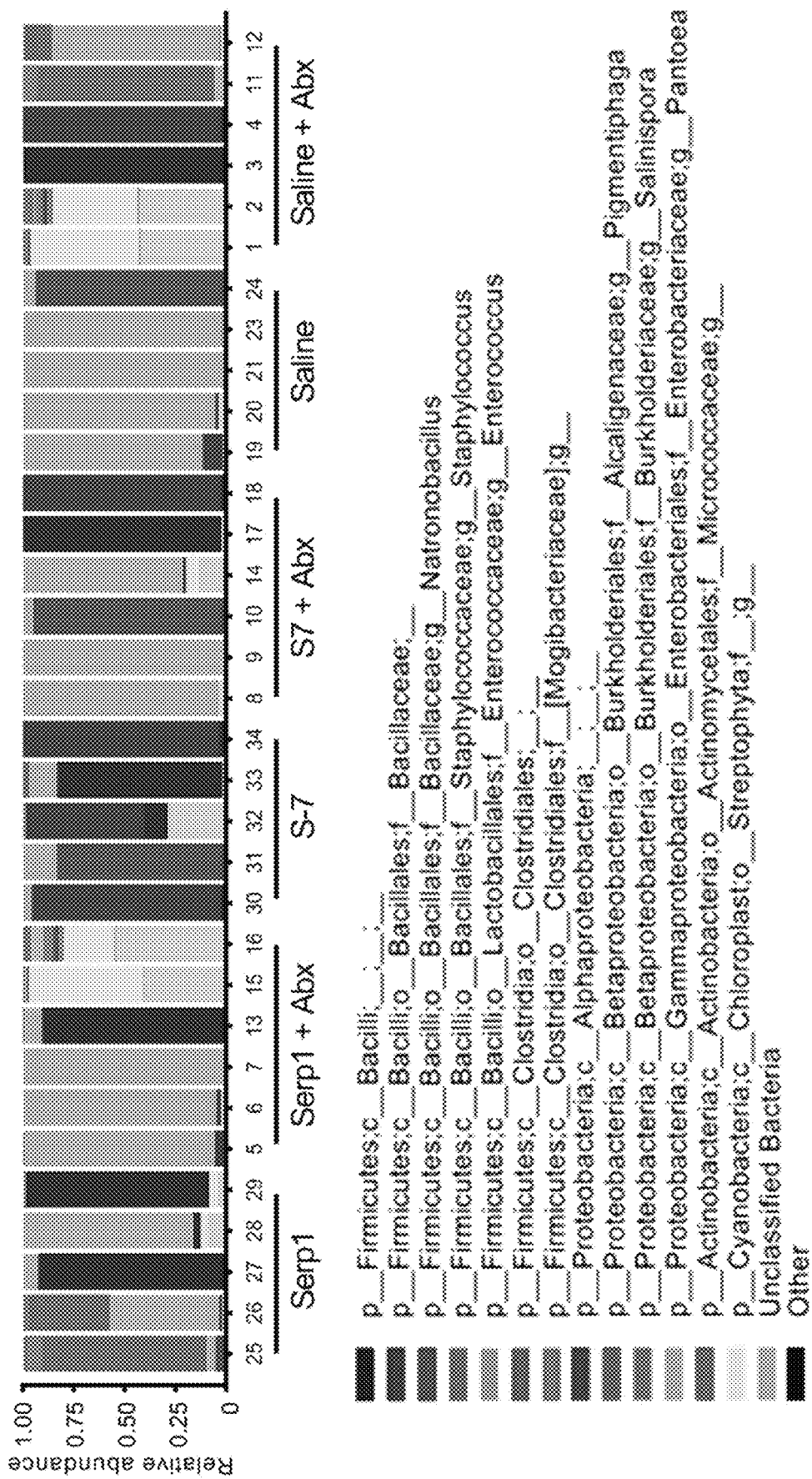
FIGS. 3A-3F relates to 16S microbiome analysis.
Figure 3B:
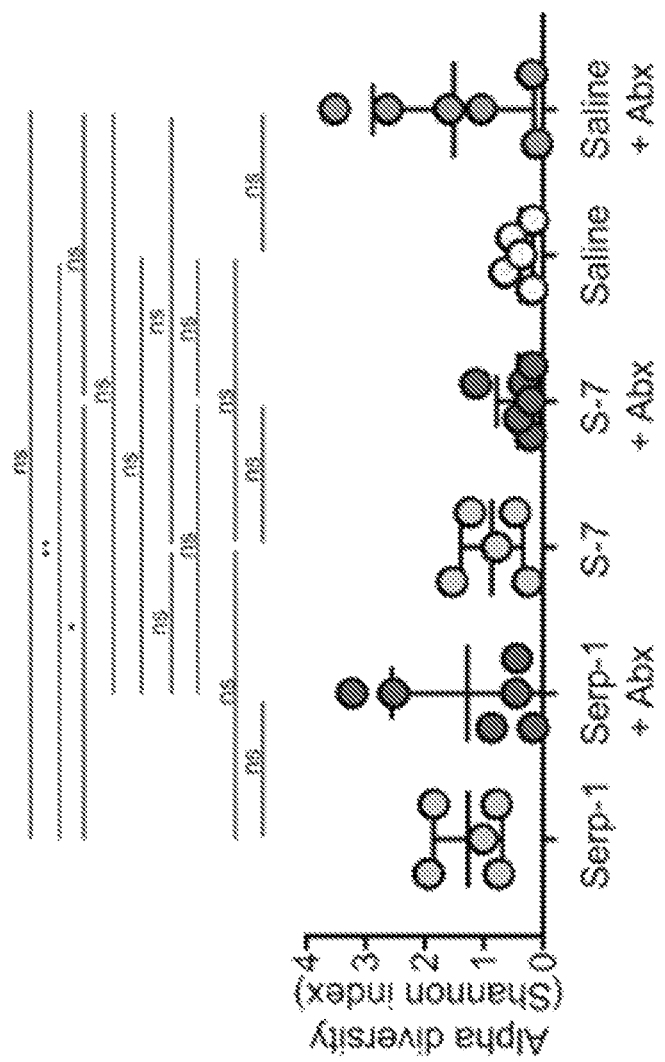
Figure 3C:
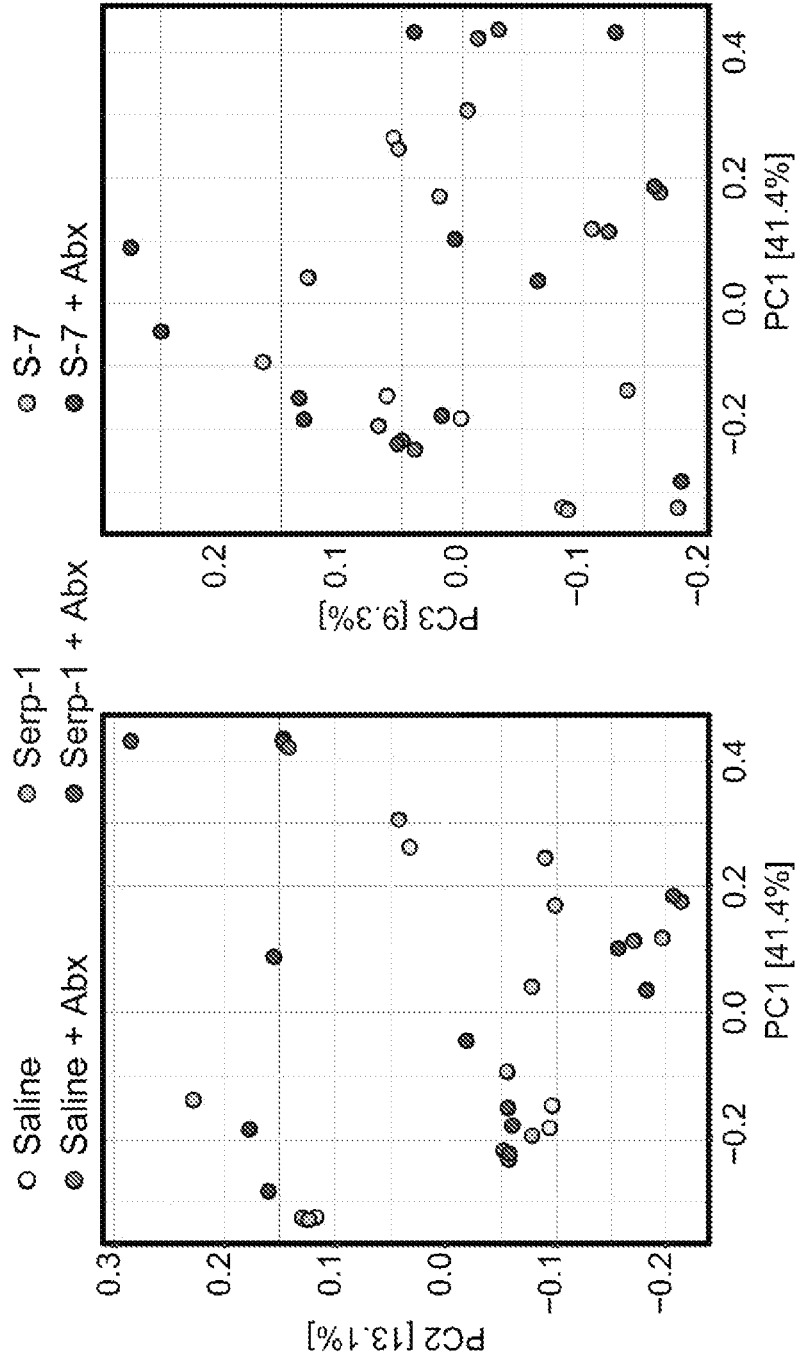

Based on the findings that (1) antibiotic-treated mice accelerated and exacerbated MHV-68 disease, reducing survival time and increasing mortality, and that (2) immune protection conferred by Serp-1 and S-7 was highly sensitive to antibiotic treatment, the gut bacterial microbiota of mice treated with Serp-1 or S-7 were profiled. 16S rRNA gene amplicon sequencing was performed on DNA extracts derived from the large intestines of individual mice 3 days post-infection with MHV-68 and after treatment with Serp-1 or S-7 (FIG. 3A). Serp-1 and S-7 treated mice, in the absence of antibiotics, had a higher diversity of microbiota (mean=1.270, p=0.0079; mean=0.862, p=0.1508) than saline treated mice (mean=0.385) (FIG. 3B). Principal coordinate analyses indicate that although the gut bacterial microbiomes of Serp-1 and S-7 treated mice differed from saline treated mice, there was variability within Serp-1 and S-7 treated mice (FIG. 3C, FIG. 7B). This finding was consistent with the phenotypic variability observed in vivo. Specifically there was partial protection by Serp-1 and S-7 treatment with 60% survival.

Figure 3D:
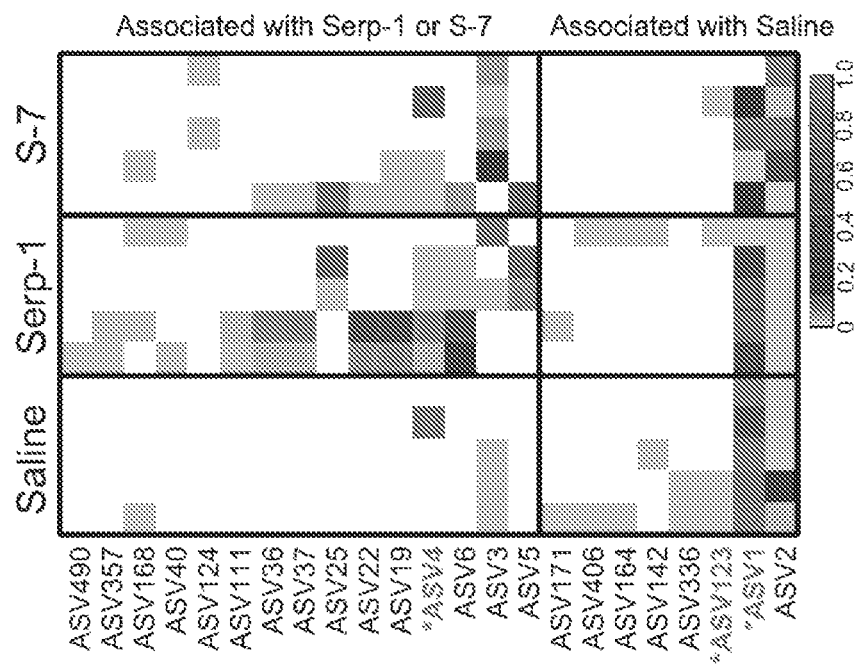
Figure 3E:
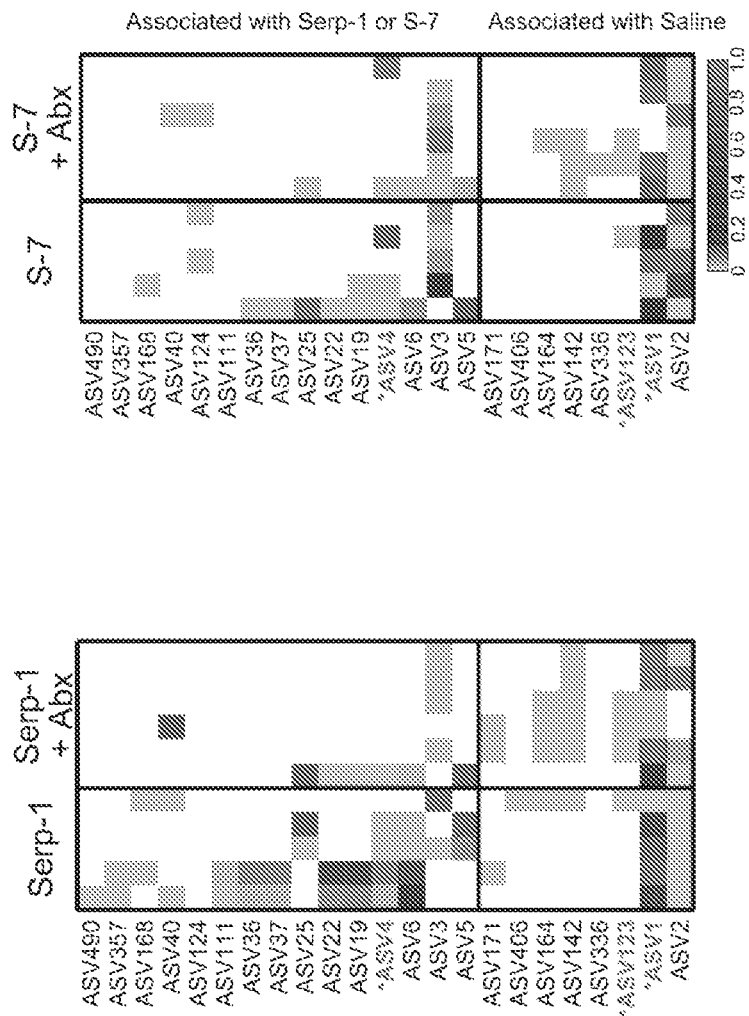
Figure 3F:
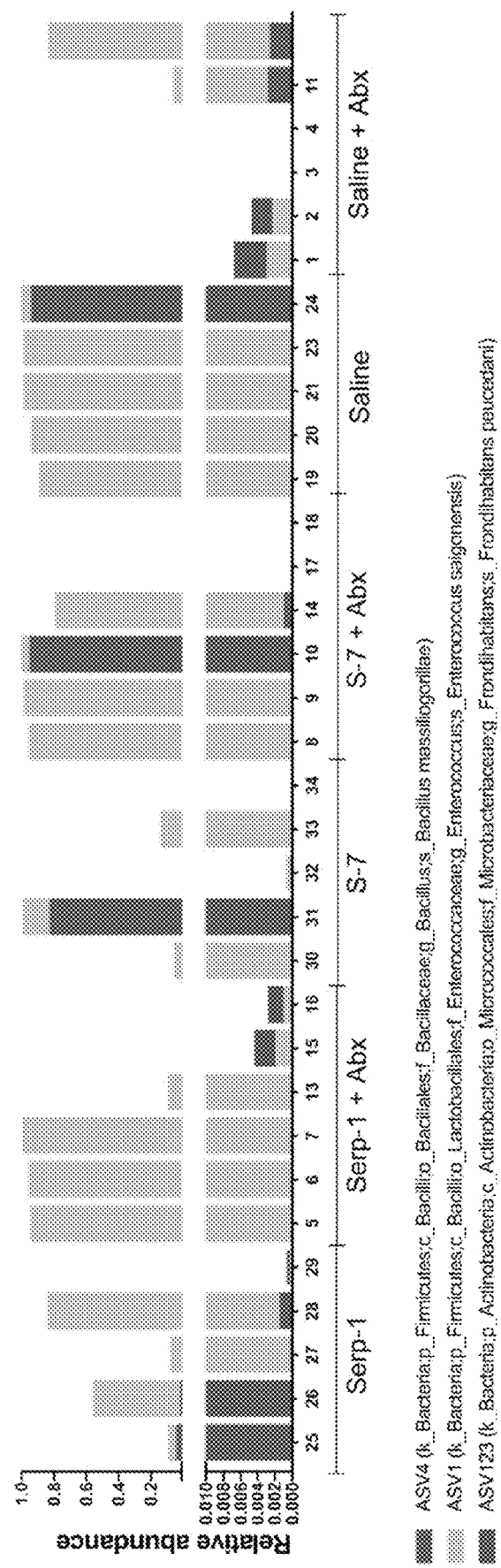

It was hypothesized that responsiveness to Serp-1 and S-7 treatment may be driven by the presence of "protective" ASVs (differentially associated with Serp-1 and/or S-7 treatment) or the absence of "potentiator" ASVs (differentially associated with saline treatment). Therefore, to identify potential microbe(s) responsible for the microbiome-mediated protection by Serp-1 and S-7, the gut bacterial microbiota was analyzed for discriminant ASVs that were differentially represented in Serp-1 and/or S-7 treated mice compared to saline treated mice, in the absence of antibiotics (FIG. 7C-7E). Of the 15 ASVs identified as differentially associated with Serp-1/peptide treatments, ASV4, was consistently associated with both Serp-1 and S-7 treatment (FIG. 3D). ASV4 was most closely-related to the sequence of *Bacillus massiliogorillae*. Conversely, ASV1 (most closely-related to *Frondihabitans peucedani*) and ASV123 (most closely-related to *Enterococcus saigonensis*) were identified from 8 ASV candidates as being associated with saline treatment when compared to both Serp-1 or S-7 treatments. Based upon the fact that Serp-1 and S-7 protected mice in an antibiotic-dependent manner, it was reasoned that the relative abundance of the discriminant ASVs would be altered in mice that were pre-treated with antibiotics. As predicted, the relative abundance of Serp-1- or S-7-associated ASVs was decreased in antibiotic pre-treated mice, albeit to a more moderate extent in S-7 (FIGS. 3E and 3F, compare "No Abx" to "+Abx"). These results indicate that the interplay between bacterial microbiota like ASV4, that are associated with a protective phenotype, and microbiota such as ASV1 and ASV123 that are associated with a patho-exacerbative phenotype, can influence the outcome of immune modulating treatments. In summary, responsiveness to immune modulating therapy in MHV-68 induced disease is associated with specific alterations in the gut bacterial microbiota.

The sequences for the ASVs are as follows:

```
ASV1
(k_Bacteria; p_Firmicutes; c_Bacilli;
o_Lactobacillales; f_Enterococcaceae;
g_Enterococcus; s_Enterococcus saigonensis):
                                  (SEQ ID NO: 7)
TACGTAGGTGGCAAGCGTTGTCCGGATTTATTGGGCGTAAAGCGAGCGCA

GGCGGTTTCTTAAGTCTGATGTGAAAGCCCCCGGCTCAACCGGGGAGGGT

CATTGGAAACTGGGAGACTTGAGTGCAGAAGAGGAGAGTGGAATTCCATG

TGTAGCGGTGAAATGCGTAGATATATGGAGGAACACCAGTGGCGAAGGCG

GCTCTCTGGTCTGTAACTGACGCTGAGGCTCGAAAGCGTGGGGAGCAAAC

AGG

ASV4
(k_Bacteria; p_Firmicutes; c_Bacilli;
o_Bacillales; f_Bacillaceae; g_Bacillus;
s_Bacillus massiliogorillae):
                                  (SEQ ID NO: 8)
TACGTAGGTGGCAAGCGTTGTCCGGATTTATTGGGCGTAAAGCGCGCGCA

GGTGGTTTCTTAAGTCTGATGTGAAAGCCCACGGCTCAACCGTGGAAGGT

CATTGGAAACTGGGAAACTTGAGTGCAGAAGAGGAAAGTGGAATTCCAAG

TGTAGCGGTGAAATGCGTAGATATTTGGAGGAACACCAGTGGCGAAGGCG

ACTTTCTGGTCTGTAACTGACACTGAGGCGCGAAAGCGTGGGGAGCAAAC

AGG

ASV123
(k_Bacteria; p_Actinobacteria; c_Actinobacteria;
o_Micrococcales; f_Microbacteriaceae;
g_Frondihabitans; s_Frondihabitans peucedani):
                                  (SEQ ID NO: 9)
TACGTAGGGTGCAAGCGTTGTCCGGAATTATTGGGCGTAAAGAGCTCGTA

GGCGGTTTGTCGCGTCTGCTGTGAAATCTGGGGGCTCAACCCCCAGCCTG

CAGTGGGTACGGGCAGACTAGAGTGCGGTAGGGGAGATTGGAATTCCTGG

TGTAGCGGTGGAATGCGCAGATATCAGGAGGAACACCGATGGCGAAGGCA

GATCTCTGGGCCGTAACTGACGCTGAGGAGCGAAAGCATGGGGAGCGAAC

AGG
```

Antibiotic-dependent exacerbation of early lung pathology of MHV-68 induced disease.

MHV-68 persistent infection leads to severe hemorrhagic and consolidating pulmonary pathology. Hence, it was investigated whether the pulmonary pathology induced by MHV-68 infection reflected the antibiotic-dependent exacerbation observed in survival analysis. Quantitative morphometric analyses of lungs were performed at an early, 3-day follow-up after infection. In the absence of antibiotics, considerable early pulmonary consolidation and inflammation was observed in MHV-68-infected lung tissue in IFNγR−/− mice treated with control saline alone. This severe pulmonary pathology was considerably reduced by Serp-1 or S-7 peptide treatment (FIG. 4A). Early lung pathology was markedly worse after antibiotic treatment in all conditions (saline, Serp-1 or S-7), with most animals in the saline group also showing hemorrhage in affected regions.

It has been demonstrated that thickening of the alveolar wall/septa and reduction of alveolar lumen area are reliable indicators of pulmonary inflammation in acute laboratory models. In the present study, quantitative morphometry of the lungs revealed a significant reduction in alveolar wall thickness in MHV-68-infected mice treated with Serp-1 or S-7 versus saline-treated controls that was lost after treatment with antibiotics (FIG. 4B). Without antibiotic pre-treatment and when compared to saline-treated controls, alveolar lumen area was significantly increased in mice treated with S-7 ($p=0.0067$) with a trend toward an increase in mice treated with Serp-1. Antibiotic treatment nullified any level of protection by treatment with S-7 (FIG. 4C). No diagnostic pathology or significant changes in inflammatory cell infiltrates on histological analysis was noted in the gut or aorta at this early, 3-day follow-up time. These results indicate that the interplay between bacterial microbiota like ASV4, that are associated with a protective phenotype, and microbiota such as ASV1 and ASV123 that are associated with a patho-exacerbative phenotype, can influence the outcome of immune modulating treatments. In summary, responsiveness to immune modulating therapy in MHV-68 induced disease is associated with specific alterations in the gut bacterial microbiota. These results indicate that immune protection against pulmonary inflammation and early stage hemorrhage promoted by Serp-1 and S-7 treatment are microbiome dependent.

Serp-1 and S-7 promote an increased gut microbiome-dependent CD3+ occupancy in the lungs.

Figure 4G:
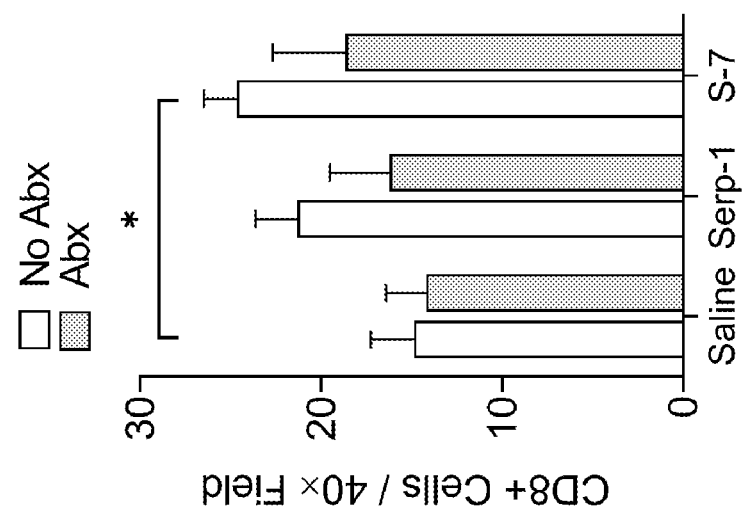

T-cell responses play a crucial role in limiting active infection and have been reported as central mediators for managing chronic MHV-68 infection. Hence, early, acute phase CD3+ T-cell recruitment to the lungs in MHV-68 infections was examined. Antibiotic treatment significantly reduced CD3+ cells in the lungs of saline-treated mice (FIG. 4E, $p=0.0155$). Further, S-7 significantly increased, and Serp-1 trended towards increasing, the detectable CD3+ cells in the lungs of infected mice (FIG. 4D,4E), indicating that the serpin-mediated protection against MHV-68 induced disease is closely associated with increased pulmonary T-cell activity. Further staining indicates no appreciable effect of Serp-1 and S-7 on pulmonary CD4+ cells (FIG. 4F), while CD8+ staining showed significant increases with S-7 (p=0.0312) and a strong trend towards increase with Serp-1 (p=0.1734) treatment (FIG. 4G). Remarkably, antibiotic treatment that depleted the gut microbiome led to a loss of this observed CD3 infiltration-promoting effects and a loss of CD8 bias of both Serp-1 and S-7 (FIG. 4E-G). Taken together, these results indicate protection from MHV-68 induced disease via CD3 recruitment and surveillance in the lungs, with a CD8 bias, enhanced by Serp-1- or S-7, proceeds via a microbiome-dependent mechanism.

Serp-1 and S-7 reduce pulmonary MHV-68 levels in a gut bacterial microbiome-dependent manner.

Figure 5A:
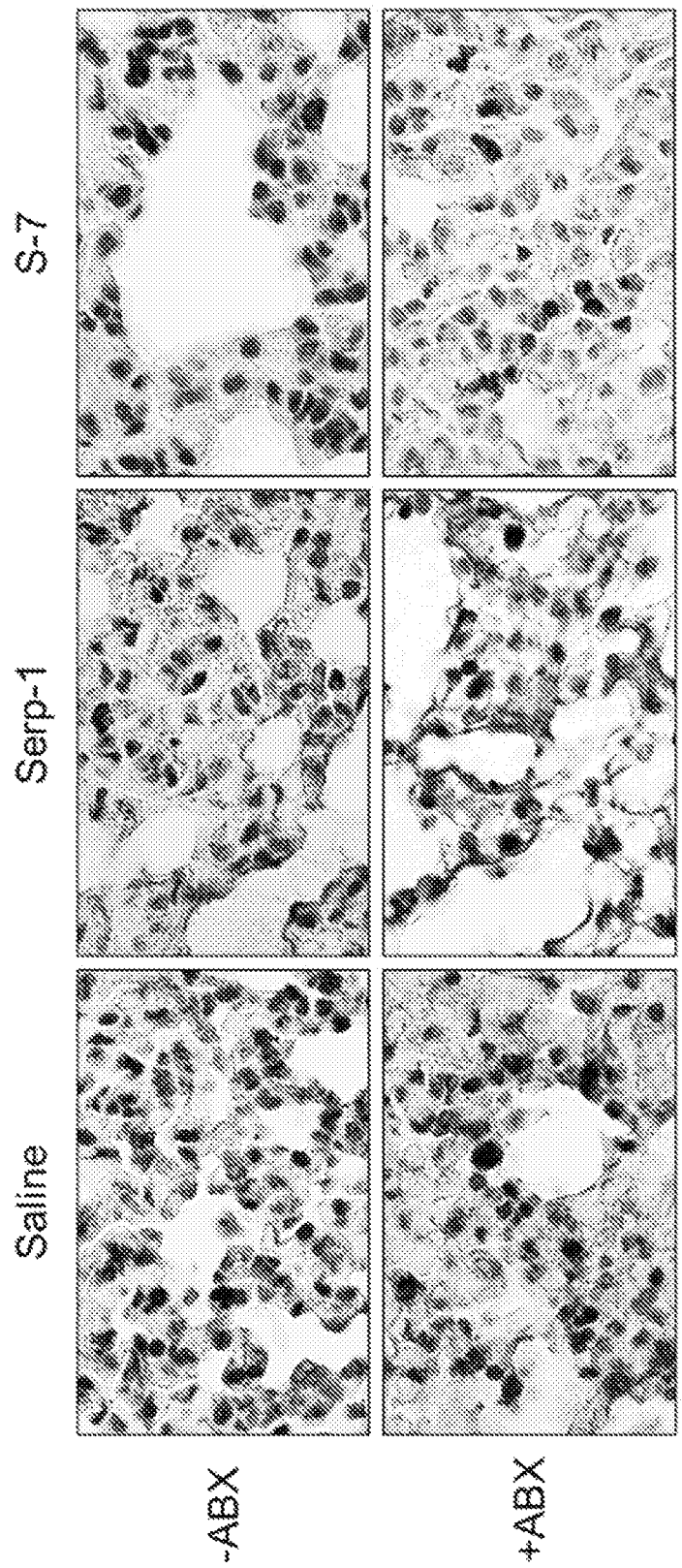
FIGS. 5A-5B illustrate Serp-1 and S-7 reduce MHV-68 presence in a gut bacterial microbiome-dependent manner.
Figure 5B:
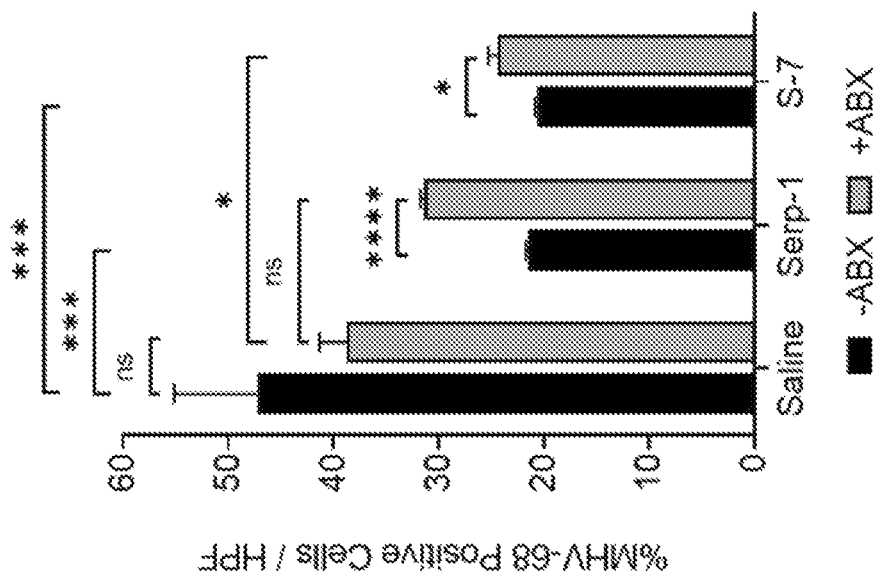
Figure 6:
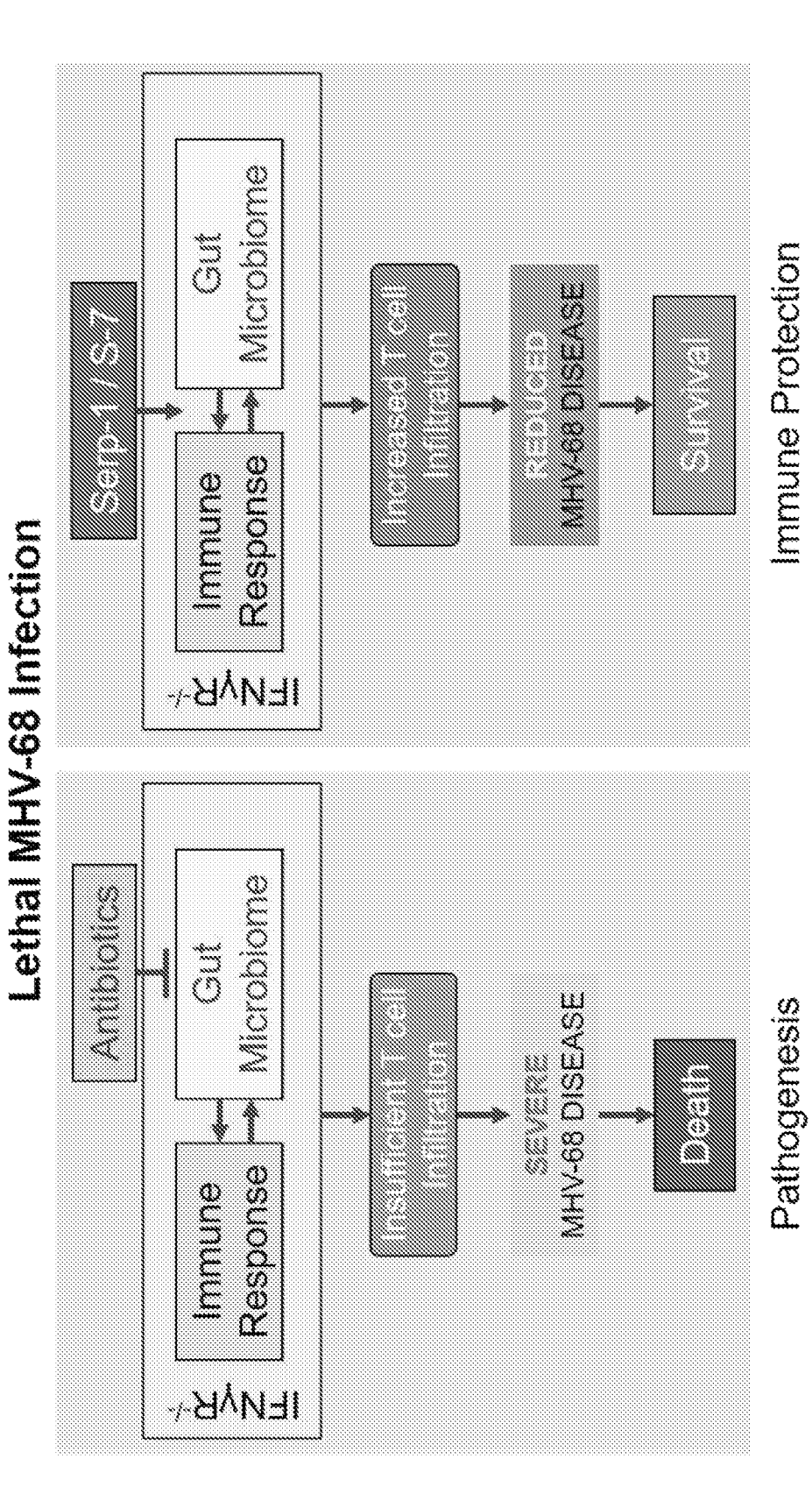
FIG. 6 is a schematic in accordance with embodiments disclosed herein. (Left Panel) In uninterrupted lethal MHV-68 infection of IFNγR$^{-/-}$ mice, the gut microbiome and immune response interact to mount an ultimately insufficient response of cells such as T-cells to affected tissues (e.g., the lungs), leading to severe disease and death. Antibiotics suppresses the immune stimulatory effects of the bacterial microbiome, reducing further the immune response and worsening the disease. (Right Panel) In immune modulator-mediated protection by treatments such as Serp-1 or S-7, the interactions leading to a sufficiently mounted immune response are enhanced, promoting an increased T-cell infiltration to affected tissues, reducing disease pathology and leading to survival.
Figure 8:
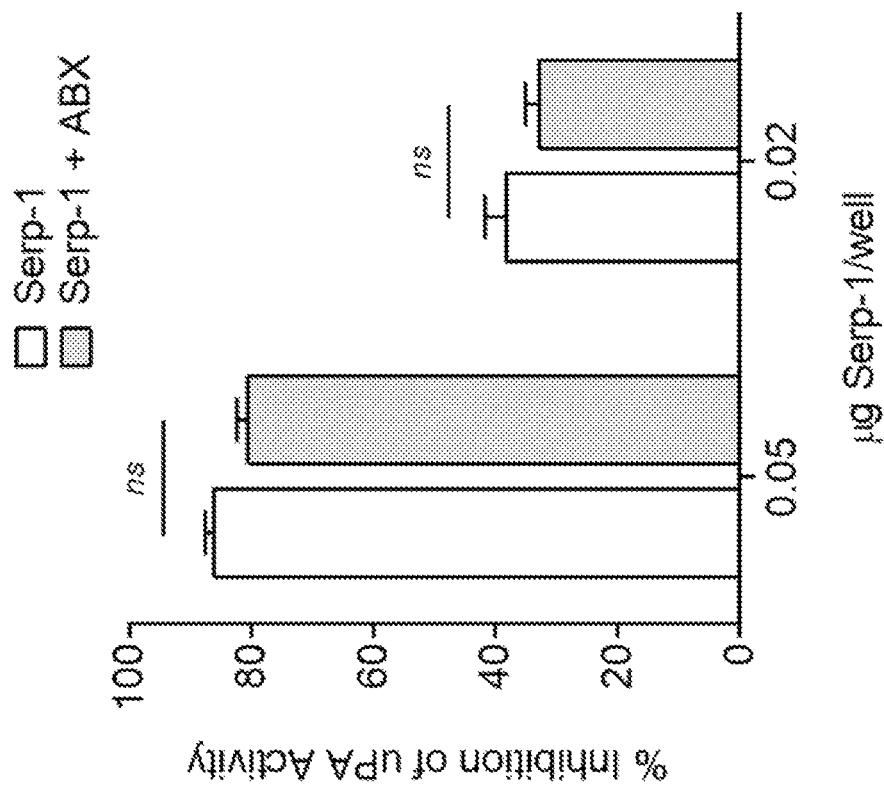
FIG. 8 is a bar graph illustrating Serp-1 inhibition of uPA activity in an in vitro substrate conversion assay is not affected by the presence of a broad-spectrum antibiotic cocktail.

Because T-cells are involved in control of MHV-68 infection, it was hypothesized that the promotion of CD3 T-cell infiltration would lead to reduced viral levels in the lungs. Antibiotic treatment did not change the amount of MHV-68 antigen staining in the lungs of mice treated with saline control alone (FIGS. 5A, 5B). However, Serp-1 and S-7 significantly reduced MHV-68 antigen levels in the lungs in mice without antibiotic treatment (FIG. 5B; Serp-1, p=0.0009; S-7, p=0.0003). These decreases in detectable MHV68 were partially reversed after antibiotic pre-treatment in MHV-68-infected mice (FIG. 5 and FIG. 8). Thus, Serp-1 and S-7 initiate a gut bacterial microbiome-dependent reduction in MHV-68 levels in the lungs.

DISCUSSION

Compelling evidence has established an important role for the gut microbiome in immune responsiveness as well as the pathogenesis of various diseases, including those with primary involvement outside of the gut, such as respiratory, hepatic, renal, neurologic, autoimmune, rheumatoid and cardiovascular conditions. Some research groups have demonstrated that targeted manipulation of the gut microbiome to correct dysbiosis, as for fecal transplants, may aid in treatment of certain diseases. For example, a small, randomized clinical trial (NCT02636647) found improved outcomes in recurrent hepatic encephalopathy patients treated by fecal microbiota transplant from a single, rationally selected donor enriched with Lachnospiraceae and Rum inococcaceae (taxa determined to be depleted in hepatic encephalopathy patients). A second trial (NTR1776) found that fecal microbiota transfer from lean donors to obese donors partially reversed symptoms of metabolic syndrome, including improvements in insulin resistance. Aside from correcting dysbiosis, recent evidence supports the hypothesis that microbiome composition also plays a significant role in determining the efficacy of some treatments. It was recently found that low gut microbiome levels of Akkermansia muciniphila caused non-responsiveness in patients receiving PD-1 blockade immunotherapy for epithelial tumors, reinforcing the importance of the microbiome in treatment efficacy, as highlighted by a critical earlier study that identified a positive correlation between *Bacteroides fragilis* and anti-CTLA4 therapy efficacy for melanoma. Alternatively, some treatments may inadvertently alter the gut microbiome and predispose to increased pathogenic infections. For example, it was recently demonstrated that proton pump inhibitors significantly reduced microbial diversity with changes in more than 20% of bacterial taxa, leading to increases in *Enterococcus, Streptococcus, Staphylococcus* and the potentially pathogenic *Escherichia coli* species. Thus, an understanding of how the gut microbiome influences, and is influenced by, new therapeutic treatments is of interest.

Trans-kingdom interactions may also play a crucial role in dictating disease pathogenesis in mammalian hosts. For viruses which require enteric bacteria for replication, antibiotics may reduce viral load. Numerous studies have demonstrated this viral-bacterial interaction in laboratory systems, such as murine and human norovirus infection. For other viruses, however, loss of the bacterial microbiome may lead to worsening clinical disease. A recent study reports that oral antibiotic (ampicillin) treatment exacerbates disease severity in flavivirus infections by modulating flavivirus-specific CD8 responses, suggesting a microbiome, immune system and virus interaction. These disparate observations, which depend substantially on (a) the virus being studied, (b) the host system and (c) the antibiotic regimen, highlight how the virome is still a poorly understood, and consequently under-appreciated, component of health and disease.

A broad-spectrum antibiotic cocktail was used to suppress the gut microbiome prior to MHV-68 infection. It was found that suppression of the gut microbiota prior to MHV-68 infection accelerated disease, with increased lethality and earlier death occurring at approximately twice the rate of untreated mice (FIG. 2C). This acceleration of MHV-68 disease was accompanied by a dramatic post-antibiotic dysbiosis and a suite of candidate ASVs with increased or decreased relative abundance associated with worsened disease outcomes.

Figure 9:
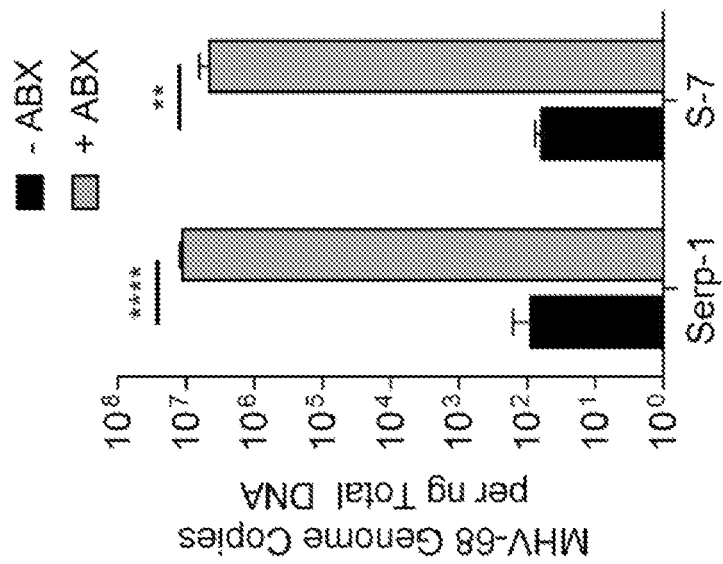
FIG. 9 is a bar graph illustrating antibiotics increases the viral load of MHV68 in the lungs.

Furthermore, the studies herein demonstrate that bacterial microbiome interactions were required for a protective immune response induced by Serp-1 or S-7. Microbiome ablation completely abolished treatment efficacy and improved survival (FIG. 1B). Probing further, it was found that Serp-1 and S-7 facilitated protection against lung inflammation and consolidation associated with an increase in CD3+ cell invasion (with a CD8+ bias) and a reduction of MHV-68 staining in the lungs (FIGS. 4 and 5). This finding indicates that T-cell surveillance (effected by CD8+ cells) is important for limiting acute GHV infection and that the loss of Serp-1-based treatment efficacy was not expected to be due to direct interactions between the antibiotics and immune modulating treatments for a number of reasons: (1) the antibiotics used in this study have a relatively short half-life (1-7 hours) and previous studies report negligible concentrations 24 hours after dosing—a timeline incorporated in this study design; (2) a rapid recovery of microbial burden within three days was observed (FIG. 2B); (3) the antibiotics in the present cocktail are not known to suppress immune responses on their own, and in some reports are observed to enhance T-cell activity; (4) it is not expected that the loss of activity is due to direct interactions with the antibiotics because in vitro inhibition of uPA activity by Serp-1 is unaffected by the presence of the same antibiotic cocktail (FIG. 9). A recent report by Yang et al. indicated that in the short-term, antibiotics can induce metabolite changes which have systemic, suppressant effects on immune function in the peritoneal space by altering respiratory activity (Yang, J. H. et al., Cell Host Microbe 22, 1-9 (2017)). Yang et al., however, utilized an *E. coli* infection and the antibiotic, ciprofloxacin, was given within 4 hours of infection and maintained during the course of the infection. Here, a gammaherpesvirus infection with longer pathogenic kinetics was used and removed antibiotics 24 hours prior to infection, wherein any trace of ciprofloxacin would be undetectable, and the inventors are not aware of any other reports suggesting immune suppressant effects of the other antibiotics in the presently utilized cocktail. Taken together, these data provide the first evidence that microbiome interactions are essential for a protective immune response, induced here by Serp-1 and S-7 treatment. We have found Serp-1 to function through the urokinase-type plasminogen activator receptor (uPAR) in systems involving immune cell infiltration (e.g., modulating levels of binding partners)essential for Serp-1 and S-7 function in MHV-68 infection.

The inventors believe that transkingdom interactions with the gut bacterial microbiome are required for host innate immunity to mount a protective response against lethal gammaherpesviral disease (FIG. 6). When MHV-68 infection causes viral pulmonary inflammation and sepsis, as induced in the MHV-68 infection model, host innate immune responses mediated by gut bacterial microbiota interactions leads to the recruitment of immune cells (e.g. T-cells) to the lungs. However, antibiotic ablation of the gut bacterial microbiota alters pathologic outcome by preventing effective immune response responses leading to acceleration of MHV-68 inflammatory pathogenesis. Immunomodulatory treatments (like Serp-1 and S-7) can induce a stronger innate immune response (such as T-cell recruitment) through (other) bacterial microbiota interactions. Thus, outcomes of GHV infection are determined by the interplay of host innate immunity and microbiota interactions.

Interestingly, the gut microbiota of all Serp-1 and S-7 treated mice did not clearly cluster separately from saline treated mice. Thus, the dynamics of selected increased or decreased microbiome ASVs is associated with worsened pathology or alternatively protective immune modulation. Specific ASVs were found that were either increased in response to Serp-1/peptide treatment (e.g. ASV4), or decreased when compared to saline treatment (e.g. ASV1 and ASV123). Taken together, these findings indicate that the responsiveness to immune modulations in MHV-68 disease involves a combination of interactions with protective microbiota and patho-exacerbative microbiota.

With this example, the pathogenicity of MHV-68 infection and effective treatment with the immune modulating serpin, Serp-1, and serpin peptide, S-7, is demonstrated to be substantially accelerated by suppression of the gut bacterial microbiome with antibiotics. MHV-68 is a model virus for studying GHV pathogenesis and severe viral sepsis, therefore this finding has implications for the pathogenesis and treatments of other GHV, such as KSHV and EBV, where adverse responses to antibiotics are clinically recognized. We further report here the modulation of gut microbiome composition by an immune modulating protein and peptide. In conclusion, (1) microbiome changes have significant impact on therapeutic immune modulating proteins and peptides, and (2), antibiotic treatment increases severity of GHV infections.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A method of reducing or inhibiting a viral or immune disorder in a subject that has acquired the viral or immune disorder, wherein the method comprises:
   detecting presence of bacteria expressing 16S rRNA comprising the sequence of Amplicon Sequence Variant 4 (ASV4) in gut microbiome of the subject; and
   administering to the subject upon detection of the presence of the bacteria expressing 16S rRNA comprising the sequence ASV4 in the subject's gut microbiome an effective amount of a composition comprising a polypeptide derived from a reactive center loop of a serine protease inhibitor or a biologically active variant thereof, and wherein the subject has not been administered antibiotics between the detection of the presence of the bacteria expressing 16S rRNA comprising the sequence ASV4 in the subject's gut microbiome and administration of the composition.

2. The method of claim 1, wherein the polypeptide comprises the amino acid sequence that is at least 95% identical to the amino acid sequence of SEQ ID NO: 2 or SEQ ID NO: 1.

3. The method of claim 1, wherein the polypeptide comprises the amino sequence that is at least 99% identical to the amino acid sequence of SEQ ID NO: 2 or SEQ ID NO: 1.

4. The method of claim 1, wherein the polypeptide has comprises the amino acid sequence GTTASSDTAITLIPR (SEQ ID NO: 2).

5. The method of claim 4, wherein the composition further comprises a carrier; and wherein the carrier is 0.9% normal saline, Citrate-buffered saline (CBS), Phosphate-buffered saline (PBS), Ringer's Lactate solution (RL), Acetated Ringer's solution (AR), 5% or 10% dextrose in normal saline (D5NS, D10NS), 5% or 10% dextrose in half-normal saline (D5HNS, D10HNS), Hank's balanced salt solution (HBSS), Earle's balanced salt solution (EBSS), Gey's balanced salt solution, tris(hydroxymethyl)aminomethane (Tris)-buffered saline (TBS), or 4-(2-hydroxyethyl)-1-piperazineethanesulfonic acid (HEPES)-buffered saline (HBS).

6. The method of claim 1, wherein said administering is via one or more of the following routes of administration selected from the group consisting of: subcutaneous, intravenous or intramuscular; and wherein the viral or immune disorder is an infection of a gammaherpesviruse (GHV), Epstein-Barr virus (EBV) and/or Kaposi's sarcoma-associated herpesvirus (KSHV).

7. The method of claim 6, wherein the GHV is murine gammaherpesvirus-68 (MHV-68); and/or the infection of GHV is acute or chronic.

8. The method of claim 1, wherein the immune disorder is an inflammatory vasculitic syndrome (IVS).

9. The method of claim 1, wherein the composition increases protective gut microbiota and/or decreases patho-exacerbative gut microbiota, wherein protective gut microbiota comprise ASV4 microbiota and patho-exacerbative gut microbiota comprise Amplicon Sequence Variant 1 (ASV1) and Amplicon Sequence Variant 123 (ASV123) microbiota.

* * * * *

SEQUENCE LISTING

```
<160> NUMBER OF SEQ ID NOS: 9

<210> SEQ ID NO 1
<211> LENGTH: 350
<212> TYPE: PRT
<213> ORGANISM: Artificial Sequence
<220> FEATURE:
<223> OTHER INFORMATION: Serp-1 recombinant polypeptide

<400> SEQUENCE: 1

Met Lys Tyr Leu Val Leu Val Leu Cys Leu Thr Ser Cys Ala Cys Arg
1               5                   10                  15

Asp Ile Gly Leu Trp Thr Phe Arg Tyr Val Tyr Asn Glu Ser Asp Asn
            20                  25                  30

Val Val Phe Ser Pro Tyr Gly Leu Thr Ser Ala Leu Ser Val Leu Arg
        35                  40                  45

Ile Ala Ala Gly Gly Asn Thr Lys Arg Glu Ile Asp Val Pro Glu Ser
    50                  55                  60

Val Val Glu Asp Ser Asp Ala Phe Leu Ala Leu Arg Glu Leu Phe Val
65                  70                  75                  80

Asp Ala Ser Val Pro Leu Arg Pro Glu Phe Thr Ala Glu Phe Ser Ser
                85                  90                  95

Arg Phe Asn Thr Ser Val Gln Arg Val Thr Phe Asn Ser Glu Asn Val
            100                 105                 110

Lys Asp Val Ile Asn Ser Tyr Val Lys Asp Lys Thr Gly Gly Asp Val
        115                 120                 125

Pro Arg Val Leu Asp Ala Ser Leu Asp Arg Asp Thr Lys Met Leu Leu
    130                 135                 140
```

```
Leu Ser Ser Val Arg Met Lys Thr Ser Trp Arg His Val Phe Asp Pro
145                 150                 155                 160

Ser Phe Thr Thr Asp Gln Pro Phe Tyr Ser Gly Asn Val Thr Tyr Lys
                165                 170                 175

Val Arg Met Met Asn Lys Ile Asp Thr Leu Lys Thr Glu Thr Phe Thr
            180                 185                 190

Leu Arg Asn Val Gly Tyr Ser Val Thr Glu Leu Pro Tyr Lys Arg Arg
        195                 200                 205

Gln Thr Ala Met Leu Leu Val Val Pro Asp Asp Leu Gly Glu Ile Val
    210                 215                 220

Arg Ala Leu Asp Leu Ser Leu Val Arg Phe Trp Ile Arg Asn Met Arg
225                 230                 235                 240

Lys Asp Val Cys Gln Val Val Met Pro Lys Phe Ser Val Glu Ser Val
                245                 250                 255

Leu Asp Leu Arg Asp Ala Leu Gln Arg Leu Gly Val Arg Asp Ala Phe
            260                 265                 270

Asp Pro Ser Arg Ala Asp Phe Gly Gln Ala Ser Pro Ser Asn Asp Leu
        275                 280                 285

Tyr Val Thr Lys Val Leu Gln Thr Ser Lys Ile Glu Ala Asp Glu Arg
    290                 295                 300

Gly Thr Thr Ala Ser Ser Asp Thr Ala Ile Thr Leu Ile Pro Arg Asn
305                 310                 315                 320

Ala Leu Thr Ala Ile Val Ala Asn Lys Pro Phe Met Phe Leu Ile Tyr
                325                 330                 335

His Lys Pro Thr Thr Thr Val Leu Phe Met Gly Thr Ile Thr
            340                 345                 350

<210> SEQ ID NO 2
<211> LENGTH: 15
<212> TYPE: PRT
<213> ORGANISM: Artificial Sequence
<220> FEATURE:
<223> OTHER INFORMATION: Reactive Center Loop Polypeptide sequence of
      for a serine protease inhibitor

<400> SEQUENCE: 2

Gly Thr Thr Ala Ser Ser Asp Thr Ala Ile Thr Leu Ile Pro Arg
1               5                   10                  15

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide primer 65F

<400> SEQUENCE: 3
gtcagggccc agtccgta                                                 18

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide primer 65R

<400> SEQUENCE: 4
tggccctcta ccttctgttg a                                             21
```

```
<210> SEQ ID NO 5
<211> LENGTH: 15
<212> TYPE: PRT
<213> ORGANISM: Artificial Sequence
<220> FEATURE:
<223> OTHER INFORMATION: Modified S-7 peptide MPS7-8

<400> SEQUENCE: 5

Gly Thr Thr Ala Ser Ser Asp Thr Ala Ile Thr Leu Glu Pro Arg
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Modified S7 peptide MPS7-9

<400> SEQUENCE: 6

Gly Thr Thr Ala Ser Ser Asp Thr Ala Ile Thr Asp Glu Pro Arg
1               5                   10                  15

<210> SEQ ID NO 7
<211> LENGTH: 253
<212> TYPE: DNA
<213> ORGANISM: Artificial Sequence
<220> FEATURE:
<223> OTHER INFORMATION: ASV1 nucleotide sequence

<400> SEQUENCE: 7
tacgtaggtg gcaagcgttg tccggattta ttgggcgtaa agcgagcgca ggcggtttct      60
taagtctgat gtgaaagccc ccggctcaac cggggagggt cattggaaac tgggagactt    120
gagtgcagaa gaggagagtg gaattccatg tgtagcggtg aaatgcgtag atatatggag    180
gaacaccagt ggcgaaggcg gctctctggt ctgtaactga cgctgaggct cgaaagcgtg    240
gggagcaaac agg                                                       253

<210> SEQ ID NO 8
<211> LENGTH: 253
<212> TYPE: DNA
<213> ORGANISM: Artificial Sequence
<220> FEATURE:
<223> OTHER INFORMATION: ASV4 nucleotide sequence

<400> SEQUENCE: 8
tacgtaggtg gcaagcgttg tccggattta ttgggcgtaa agcgcgcgca ggtggtttct      60
taagtctgat gtgaaagccc acggctcaac cgtggaaggt cattggaaac tgggaaactt    120
gagtgcagaa gaggaaagtg gaattccaag tgtagcggtg aaatgcgtag atatttggag    180
gaacaccagt ggcgaaggcg actttctggt ctgtaactga cactgaggcg cgaaagcgtg    240
gggagcaaac agg                                                       253

<210> SEQ ID NO 9
<211> LENGTH: 253
<212> TYPE: DNA
<213> ORGANISM: Artificial Sequence
<220> FEATURE:
<223> OTHER INFORMATION: ASV123 nucleotide sequence

<400> SEQUENCE: 9
tacgtagggt gcaagcgttg tccggaatta ttgggcgtaa agagctcgta ggcggtttgt      60
cgcgtctgct gtgaaatctg ggggctcaac ccccagcctg cagtgggtac gggcagacta    120
```

```
gagtgcggta ggggagattg gaattcctgg tgtagcggtg gaatgcgcag atatcaggag      180
gaacaccgat ggcgaaggca gatctctggg ccgtaactga cgctgaggag cgaaagcatg      240
gggagcgaac agg                                                         253
```